(12) United States Patent
Nakano et al.

(10) Patent No.: US 11,391,194 B2
(45) Date of Patent: Jul. 19, 2022

(54) GAS SENSOR CONTROL APPARATUS, GAS SENSOR APPARATUS, AND INTERNAL COMBUSTION ENGINE CONTROL APPARATUS

(71) Applicant: NGK SPARK PLUG CO., LTD., Nagoya (JP)

(72) Inventors: Yoshihiro Nakano, Nagoya (JP); Kimihiro Kohama, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 142 days.

(21) Appl. No.: 17/016,722

(22) Filed: Sep. 10, 2020

(65) Prior Publication Data
US 2021/0079828 A1 Mar. 18, 2021

(30) Foreign Application Priority Data

Sep. 13, 2019 (JP) .............................. JP2019-166843
Jul. 22, 2020 (JP) .............................. JP2020-125048

(51) Int. Cl.
*F01N 11/00* (2006.01)
*F02D 41/14* (2006.01)
(Continued)

(52) U.S. Cl.
CPC .......... *F01N 11/007* (2013.01); *F02D 41/145* (2013.01); *F02D 41/1438* (2013.01);
(Continued)

(58) Field of Classification Search
CPC .............. G01N 27/409; G01N 33/0054; F01N 11/007; F02D 41/1438; F02D 41/1448;
(Continued)

(56) References Cited

U.S. PATENT DOCUMENTS

2009/0266142 A1* 10/2009 Wang ................. G01N 33/0054
73/23.32
2011/0023855 A1* 2/2011 Van Nieuwstadt ... F01N 13/009
123/703
(Continued)

FOREIGN PATENT DOCUMENTS

JP 2015-034814 A 2/2015
JP 2018-072315 A 5/2018

*Primary Examiner* — Erick R Solis
(74) *Attorney, Agent, or Firm* — Sughrue Mion, PLLC

(57) ABSTRACT

A gas sensor control apparatus (300) including a control section (61) which executes a first receiving process (STEP 1) for receiving a first detection result output from a mixed-potential-type ammonia detection section (42) for detecting ammonia contained in a gas under measurement and corresponding to the concentration of ammonia, a second receiving process (STEP 1) for receiving a second detection result output from an oxygen detection section (2) for detecting oxygen contained in the gas under measurement and corresponding to the concentration of oxygen, a first concentration calculation process (STEP 3) for calculating a first ammonia concentration of the gas under measurement based on the first detection result and the second detection result, and a pressure correction process (STEP 6) for correcting the first ammonia concentration based on pressure information obtained from an external device (220), thereby obtaining a second ammonia concentration of the gas under measurement.

9 Claims, 13 Drawing Sheets

(51) Int. Cl.
*G01N 33/00* (2006.01)
*G01N 27/409* (2006.01)
*G01N 27/41* (2006.01)
*G01N 27/407* (2006.01)

(52) U.S. Cl.
CPC ....... *F02D 41/1454* (2013.01); *G01N 27/409* (2013.01); *G01N 27/4071* (2013.01); *G01N 27/41* (2013.01); *G01N 33/0037* (2013.01); *G01N 33/0054* (2013.01); *F02D 2041/1468* (2013.01); *F02D 2041/1469* (2013.01)

(58) Field of Classification Search
CPC ............... F02D 41/145; F02D 41/1454; F02D 2041/1468; F02D 2041/1469
USPC ........... 701/109; 123/676; 73/114.71, 114.73
See application file for complete search history.

(56) References Cited

U.S. PATENT DOCUMENTS

| | | | |
|---|---|---|---|
| 2012/0055139 A1* | 3/2012 | Aichhorn | F01N 3/208 73/23.31 |
| 2015/0013431 A1 | 1/2015 | Kakimoto et al. | |
| 2015/0086426 A1* | 3/2015 | DeGeorge | F01N 3/025 422/119 |
| 2016/0348553 A1* | 12/2016 | Lee | F02D 41/1454 |
| 2018/0112582 A1 | 4/2018 | Okamoto et al. | |
| 2018/0113103 A1 | 4/2018 | Okamoto et al. | |
| 2020/0003725 A1* | 1/2020 | Nakagaki | G01N 27/4077 |
| 2020/0200700 A1* | 6/2020 | Okamoto | G01N 27/4075 |
| 2021/0208095 A1* | 7/2021 | Ichikawa | G01N 27/4175 |
| 2022/0011260 A1* | 1/2022 | Onishi | G01M 15/102 |

* cited by examiner

GAS SENSOR CONTROL APPARATUS, GAS SENSOR APPARATUS, AND INTERNAL COMBUSTION ENGINE CONTROL APPARATUS

BACKGROUND OF THE INVENTION

1. Field of the Invention

The present invention relates to a gas sensor control apparatus, a gas sensor apparatus, and an internal combustion engine control apparatus.

2. Description of the Related Art

An ammonia sensor for detecting the concentration of ammonia contained in a gas under measurement (for example, exhaust gas discharged from an internal combustion engine) has been known (see, for example, Patent Document 1). An ammonia sensor of such a type includes a mixed-potential cell having a solid electrolyte layer and a pair of electrodes (a detection electrode and a reference electrode). Although the mixed-potential cell outputs an electromotive force corresponding to the ammonia concentration in the gas under measurement, the oxygen concentration in the gas under measurement is also reflected in the electromotive force.

For example, Patent Document 2 shows a known relational expression representing the relation among the ammonia concentration in the gas under measurement, the oxygen concentration in the gas under measurement, and the electromotive force of the mixed-potential cell. The ammonia concentration in the gas under measurement is calculated based on information representing the electromotive force of the mixed-potential cell and the oxygen concentration in the gas under measurement, respectively, and through use of such a relational expression.

[Patent Document 1] Japanese Patent Application Laid-Open (kokai) No. 2015-34814

[Patent Document 2] Japanese Patent Application Laid-Open (kokai) No. 2018-72315

3. Problem to be Solved by the Invention

The pressure of the gas under measurement is not constant at all times but may change. For example, when a throttle valve for adjusting the amount of air taken into an internal combustion engine is fully opened, the pressure of exhaust gas from the internal combustion engine (the gas under measurement) increases.

The inventors of the present invention found that a change in the pressure of the gas under measurement leads to a change in the output (electromotive force) of the mixed-potential cell. In the conventional ammonia sensor, the influence of the pressure of the gas under measurement has not been taken into consideration for determining the ammonia concentration.

The present inventors found that when the pressure of the gas under measurement changes, the output (electromotive force) of a mixed-potential-type ammonia detection section changes (i.e., the output of the mixed-potential-type ammonia detection section is influenced by the pressure of the gas under measurement). Presumably, the cause of such a phenomenon is as follows.

As shown in Patent Document 2, at the detection electrode of a mixed-potential cell, an anode reaction and a cathode reaction occur concurrently. In the anode reaction, ammonia ($2/3$ $NH_3$) reacts with oxygen ions ($O^{2-}$), whereby nitrogen ($1/3$ $N_2$), water ($H_2O$), and electrons (2 $e^-$) are produced. In the cathode reaction, oxygen ($1/2$ $O_2$) reacts with electrons (2 $e^-$), whereby oxygen ions ($O^{2-}$) are produced. The equilibrium point of the anode reaction in relation to the cathode reaction is observed as an electromotive force of the mixed-potential cell. In such a state, for example, when the pressure of the gas under measurement increases, the electromotive force of the mixed-potential cell becomes smaller. Conceivably, such a phenomenon occurs because when the pressure of the gas under measurement increases, the apparent oxygen concentration becomes higher. As a result, presumably, the detection electrode of the mixed-potential cell reacts with oxygen more easily, and the cathode reaction occurs more easily as compared with the anode reaction.

SUMMARY OF THE INVENTION

It is therefore an object of the present invention to provide a gas sensor control apparatus, a gas sensor apparatus, and an internal combustion engine control apparatus which improve the accuracy in measuring ammonia concentration by mitigating the influence of the pressure of the gas under measurement.

The above object has been achieved by providing, in a first aspect of the invention (1), a gas sensor control apparatus comprising a control section that executes: a first receiving process for receiving a first detection result output from a mixed-potential-type ammonia detection section for detecting ammonia contained in a gas under measurement, the first detection result corresponding to the concentration of the ammonia, a second receiving process for receiving a second detection result output from an oxygen detection section for detecting oxygen contained in the gas under measurement, the second detection result corresponding to the concentration of the oxygen, a first concentration calculation process for calculating, as a first ammonia concentration, the concentration of ammonia contained in the gas under measurement based on the first detection result and the second detection result, and a pressure correction process for correcting the first ammonia concentration, based on pressure information obtained from an external device and representing pressure of the gas under measurement, so as to mitigate an influence of pressure of the gas under measurement on the first ammonia concentration, thereby obtaining a second ammonia concentration of the gas under measurement.

In a preferred embodiment (2) of the gas sensor control apparatus (1) above, wherein the pressure correction process is a process for obtaining the second ammonia concentration by correcting the first ammonia concentration using a correction coefficient based on the pressure information.

In another preferred embodiment (3) of the gas sensor control apparatus (1) or (2) above, wherein, when the detected oxygen concentration is influenced by the pressure of the gas under measurement, the control section executes an oxygen pressure correction process for correcting the second ammonia concentration based on the pressure information representing the pressure of the gas under measurement so as to mitigate an influence of the pressure, thereby obtaining a third ammonia concentration of the gas under measurement.

In yet another preferred embodiment (4) of the gas sensor control apparatus of any of (1) to (3) above, wherein, when the detected oxygen concentration is influenced by the pressure of the gas under measurement, the control section executes, instead of the pressure correction process, a simultaneous correction process for correcting the first ammonia concentration based on the pressure information representing the pressure of the gas under measurement so as to mitigate an influence of the pressure of the gas under measurement on the first ammonia concentration and an influence of the pressure of the gas under measurement on the detected oxygen concentration, thereby obtaining a fourth ammonia concentration of the gas under measurement.

In a second aspect, the present invention provides (5), a gas sensor apparatus comprising: a mixed-potential-type ammonia detection section for detecting ammonia contained in a gas under measurement; an oxygen detection section for detecting oxygen contained in the gas under measurement; and a gas sensor control apparatus as described in any of (1) to (4) above.

In a third aspect, the invention (6) provides, an internal combustion engine control apparatus for controlling an operation state of an internal combustion engine, the internal combustion engine control apparatus comprising a control section that executes: a first receiving process for receiving a first detection result output from a mixed-potential-type ammonia detection section for detecting ammonia contained in a gas under measurement discharged from the internal combustion engine, the first detection result corresponding to the concentration of the ammonia detected by the mixed-potential-type ammonia detection section, a second receiving process for receiving a second detection result output from an oxygen detection section for detecting oxygen contained in the gas under measurement, the second detection result corresponding to the concentration of the oxygen, a first concentration calculation process for calculating, as a first ammonia concentration, the concentration of ammonia contained in the gas under measurement based on the first detection result and the second detection result, and a pressure correction process for correcting the first ammonia concentration, based on pressure information obtained from an external device and representing pressure of the gas under measurement, so as to mitigate an influence of pressure of the gas under measurement on the first ammonia concentration, thereby obtaining a second ammonia concentration of the gas under measurement.

In a preferred embodiment (7) of the internal combustion engine control apparatus (6) above, wherein the pressure correction process is a process for obtaining the second ammonia concentration by correcting the first ammonia concentration using a correction coefficient based on the pressure information.

In another preferred embodiment (8) of the internal combustion engine control apparatus of (6) or (7) above, wherein, when the detected oxygen concentration is influenced by the pressure of the gas under measurement, the control section executes an oxygen pressure correction process for correcting the second ammonia concentration based on the pressure information representing the pressure of the gas under measurement so as to mitigate an influence of the pressure, thereby obtaining a third ammonia concentration of the gas under measurement.

In another preferred embodiment (9) of the internal combustion engine control apparatus of any of (6) to (8) above, wherein, when the detected oxygen concentration is influenced by the pressure of the gas under measurement, the control section executes, instead of the pressure correction process, a simultaneous correction process for correcting the first ammonia concentration based on the pressure information representing the pressure of the gas under measurement so as to mitigate an influence of the pressure of the gas under measurement on the first ammonia concentration and an influence of the pressure of the gas under measurement on the detected oxygen concentration, thereby obtaining a fourth ammonia concentration of the gas under measurement.

Effect of the Invention

According to the invention, in the gas sensor control apparatus, the gas sensor apparatus, and the internal combustion engine control apparatus, the accuracy in detecting the ammonia concentration can be improved by mitigating the influence of the pressure of the gas under measurement.

DESCRIPTION OF REFERENCE NUMERALS

Figure 1:
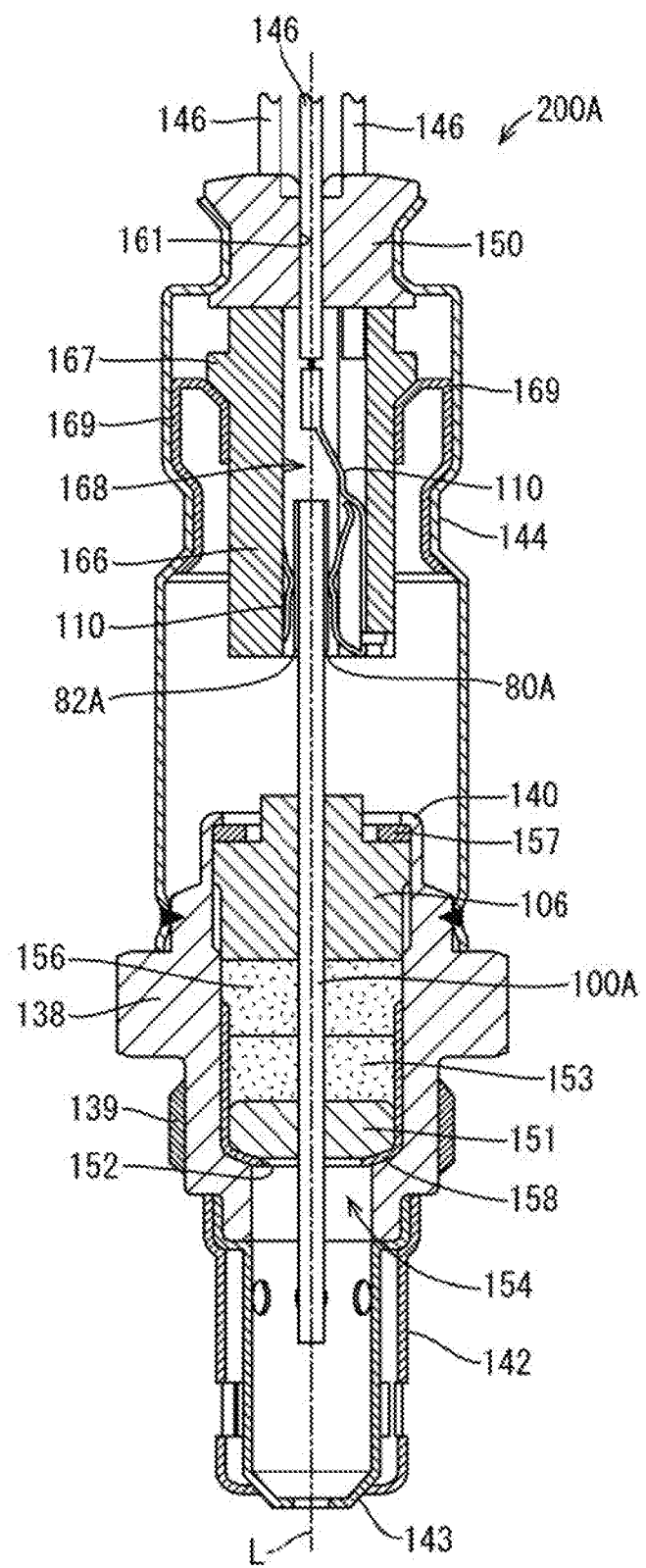
FIG. 1 is a sectional view of a multi-gas sensor according to a first embodiment taken along a longitudinal direction thereof.

Reference numerals used to identify various features in the drawings include the following.

2: first pumping cell (oxygen detection section), 42: ammonia sensor section (ammonia detection section), 42$x$: first ammonia sensor section, 42$y$: second ammonia sensor section, 60: microcomputer (SCU), 61: CPU (control section), 100A: multi-gas sensor element, 200A: multi-gas sensor, 220: ECU, 221: ECU (internal combustion engine control apparatus), 222: CPU (control section), 300: gas sensor control apparatus, 400: multi-gas sensor apparatus (gas sensor apparatus), 500: pressure sensor, 600: internal combustion engine control system, L: axial line

DETAILED DESCRIPTION OF THE PREFERRED EMBODIMENT

The present invention will now be described in greater detail with reference to the drawings. However, the invention should not be construed as being limited thereto.

First Embodiment

A first embodiment of the present invention will now be described with reference to FIGS. 1 to 5. In the present embodiment, a process for detecting the ammonia concentration in exhaust gas (an example of the gas under measurement) is performed in a gas sensor control apparatus 300 provided in a multi-gas sensor apparatus (an example of the gas sensor apparatus) 400.

Figure 2:
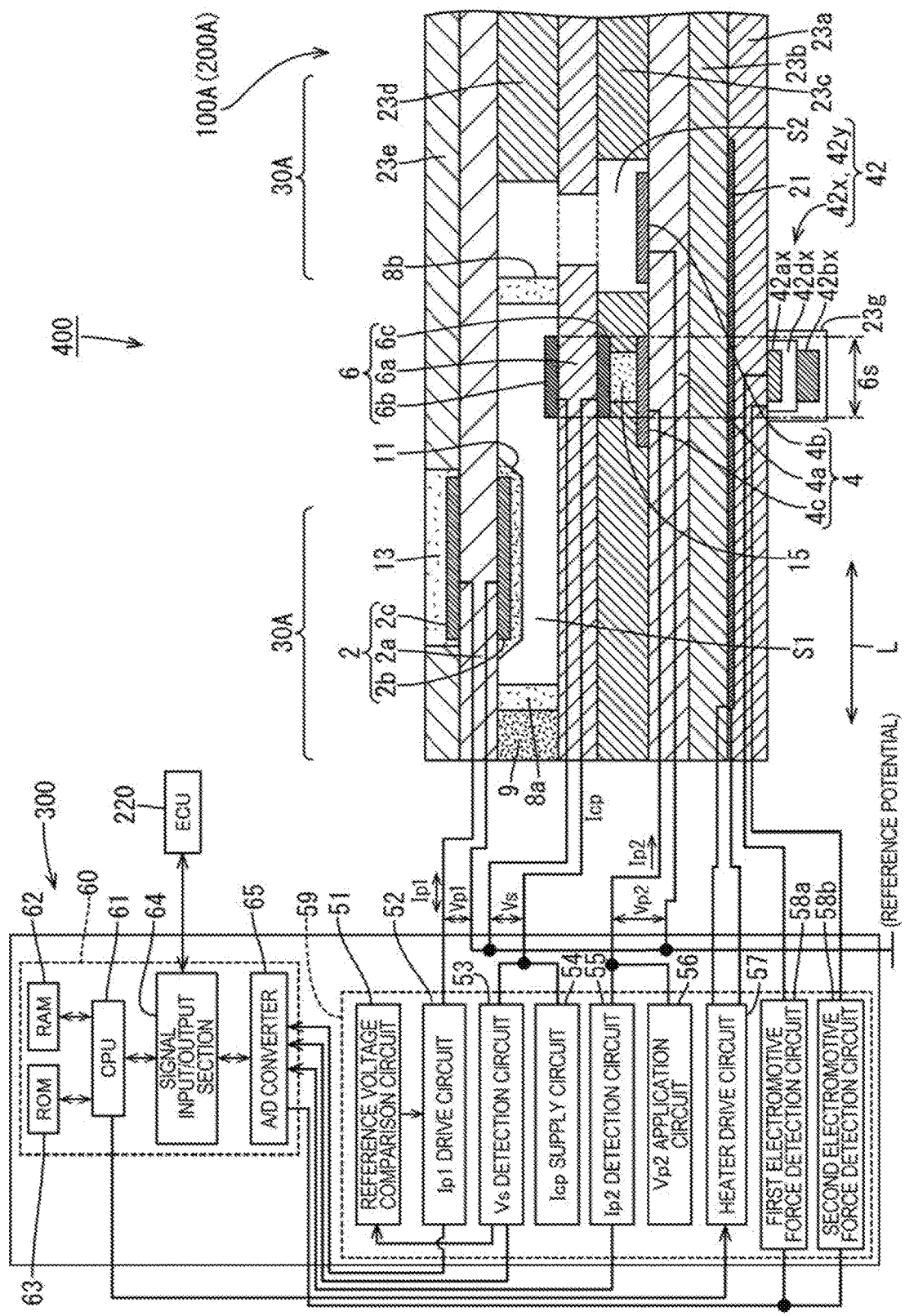
FIG. 2 is an explanatory diagram schematically showing the configuration of a multi-gas sensor apparatus.

FIG. 1 is a sectional view of a multi-gas sensor 200A according to the first embodiment taken along a longitudinal direction thereof (the direction of an axial line L). FIG. 2 is an explanatory diagram schematically showing the configuration of the multi-gas sensor apparatus 400 according to the first embodiment. Notably, in FIG. 2, for explanatory convenience, only the longitudinal cross section (along the direction of the axial line L) of a multi-gas sensor element 100A accommodated in the multi-gas sensor 200A is shown.

The multi-gas sensor apparatus 400 is used in a urea SCR (selective catalytic reduction) system for removing nitrogen oxides (NOx) contained in exhaust gas (an example of the gas under measurement) discharged from a diesel engine (an example of the internal combustion engine) of an automobile. The urea SCR system reduces the nitrogen oxides (NOx) to nitrogen ($N_2$) through a chemical reaction between ammonia ($NH_3$) and the nitrogen oxides, thereby removing the nitrogen oxides contained in the exhaust gas. In the urea SCR system, when the amount of ammonia supplied to the nitrogen oxides becomes excessive, unreacted ammonia may be discharged to the outside in a state in which the unreacted ammonia is contained in the exhaust gas. The multi-gas sensor apparatus 400 measures the concentration of ammonia contained in the exhaust gas (the gas under measurement) in order to monitor such discharge of ammonia. Notably, as described below, the multi-gas sensor apparatus 400 is configured to measure not only the concentration of ammonia but also the concentration of NOx, etc.

The multi-gas sensor apparatus 400 includes the multi-gas sensor 200A and the gas sensor control apparatus (controller) 300.

As shown in FIG. 1, the multi-gas sensor 200A is an assembly including the multi-gas sensor element 100A for detecting the concentration of ammonia and the concentration of NOx.

The multi-gas sensor 200A includes the multi-gas sensor element 100A, a metallic shell 138, a ceramic sleeve 106, an insulating contact member 166, and a plurality of connection terminals 110 (only two of them are shown in FIG. 1). The multi-gas sensor element 100A has a plate-like shape and extends in the direction of the axial line L. The metallic shell 138 has a tubular shape and has a threaded portion 139 formed on an outer surface thereof and used for fixing to the exhaust pipe. The ceramic sleeve 106 has a tubular shape and is disposed to surround the circumference of the multi-gas sensor element 100A. The insulating contact member 166 has a contact insertion hole 168 extending therethrough in the direction of the axial line L and is disposed in such a manner that the wall surface of the contact insertion hole 168 surrounds the circumference of a rear end portion of the multi-gas sensor element 100A. The connection terminals 110 are disposed between the multi-gas sensor element 100A and the insulating contact member 166.

The metallic shell 138 has a generally tubular shape, has a through hole 154 extending therethrough in the direction of the axial line L, and has a ledge portion 152 projecting inward in the radial direction of the through hole 154. The metallic shell 138 holds the multi-gas sensor element 100A in such a manner that the forward end of the multi-gas sensor element 100A is located on the forward end side and external of the through hole 154, and electrode terminal portions 80A and 82A of the multi-gas sensor element 100A are located on the rear end side and external of the through hole 154. The ledge portion 152 is formed to have an inward taper surface which inclines in relation to a plane perpendicular to the direction of the axial line L.

An annular ceramic holder 151, powder charged layers 153 and 156 (hereinafter also referred to as talc rings 153 and 156), and the above-described ceramic sleeve 106 are stacked in the through hole 154 of the metallic shell 138 in this order from the forward end side toward the rear end side, so that these members surround the circumference of the multi-gas sensor element 100A. Also, a crimp packing 157 is disposed between the ceramic sleeve 106 and a rear end portion 140 of the metallic shell 138, and a metallic holder 158 is disposed between the ceramic holder 151 and the ledge portion 152 of the metallic shell 138. The metallic holder 158 holds the talc ring 153 and the ceramic holder 151 and maintains gastightness. Notably, the rear end portion 140 of the metallic shell 138 is crimpled so as to press the ceramic sleeve 106 toward the forward end side via the crimp packing 157.

Meanwhile, a double protector is attached to the outer circumference of a forward-end-side (lower-side in FIG. 1) portion of the metallic shell 138 by, for example, welding so as to cover the protruding portion of the multi-gas sensor element 100A. The double protector is composed of an outer protector 142 and an inner protector 143 which are made of a metal (e.g., stainless steel) and have a plurality of holes.

An outer casing 144 is fixed to the outer circumference of a rear end portion of the metallic shell 138. Also, a grommet 150 is disposed in a rear-end-side (upper-side in FIG. 1) opening of the outer casing 144. The grommet 150 has lead wire insertion holes 161 into which a plurality of lead wires 146 (only three lead wires are shown in FIG. 1) are inserted. The lead wires 146 are electrically connected to the electrode terminal portions 80A and 82A of the multi-gas sensor element 100A. Notably, for simplification, in FIG. 1, the electrode terminal portions on the front and back surfaces of the multi-gas sensor element 100A are collectively denoted by reference numerals 80A and 82A, respectively. However, in actuality, a plurality of electrode terminal portions are formed on each of the front and back surfaces of the multi-gas sensor element 100A, and the number of the electrode terminal portions corresponds to the number of electrodes of an NOx sensor section 30A and first and second ammonia sensor sections 42x and 42y, etc., described below.

The insulating contact member 166 is disposed on the rear-end side (the upper side in FIG. 1) of the multi-gas sensor element 100A protruding from the rear end portion 140 of the metallic shell 138. The insulating contact member 166 is disposed around the electrode terminal portions 80A and 82A formed on the front and back surfaces of a rear end portion of the multi-gas sensor element 100A. The insulating contact member 166 is formed into a tubular shape with the contact insertion hole 168 extending therethrough in the direction of the axial line L and has a flange portion 167 protruding radially outward from the outer surface of the insulating contact member 166. The flange portion 167 abuts against the outer casing 144 through a holding member 169, whereby the insulating contact member 166 is held inside the outer casing 144. The connection terminals 110 on the insulating contact member 166 side are electrically connected to the electrode terminal portions 80A and 82A of the multi-gas sensor element 100A, so that the electrode terminal portions 80A and 82A electrically communicate with an external device through the lead wires 146.

As shown in FIG. 2, the gas sensor control apparatus 300 is electrically connected to an ECU (engine control unit) 220. Ends of the lead wires 146 extending from the multi-gas sensor 200A are connected to a connector, and the connector is electrically connected to a connector provided on the gas sensor control apparatus 300.

Next, the structure of the multi-gas sensor element 100A provided in the multi-gas sensor 200A will be described. The multi-gas sensor element 100A includes the ammonia sensor section 42 and the NOx sensor section 30A having the same structure as a known NOx sensor.

The NOx sensor section 30A includes an NOx detection portion mainly including a first pumping cell 2, an oxygen concentration detection cell 6, and a second pumping cell 4. The NOx sensor section 30A has a structure including an insulating layer 23e, a first solid electrolyte layer 2a, an insulating layer 23d, a third solid electrolyte layer 6a, an insulating layer 23c, a second solid electrolyte layer 4a, and insulating layers 23b and 23a, which are stacked in this order. As shown in FIG. 2, a first measurement chamber S1 is formed between the first solid electrolyte layer 2a and the third solid electrolyte layer 6a. The exhaust gas is externally introduced into the first measurement chamber S1 through a first diffusion resistor element 8a disposed at the left end (inlet) of the first measurement chamber S1. Notably, a protection layer 9 formed of a porous material is disposed on the outer side of the first diffusion resistor element 8a.

A second diffusion resistor element 8b is disposed at an end of the first measurement chamber S1 opposite the inlet. A second measurement chamber S2 is formed on the right side of the first measurement chamber S1 in FIG. 2. The second measurement chamber S2 communicates with the first measurement chamber S1 through the second diffusion resistor element 8b. The second measurement chamber S2 is formed between the first solid electrolyte layer 2a and the second solid electrolyte layer 4a and penetrates the third solid electrolyte layer 6a.

An elongated heating resistor element 21 extending along the longitudinal direction of the multi-gas sensor element 100A is embedded between the insulating layers 23b and 23a. The heating resistor element 21 has a heat generating portion provided on the forward end side in the axial direction (the longitudinal direction), and a pair of lead portions extending from the heat generating portion toward the rear end side in the axial direction. The heating resistor element 21 and the insulating layers 23b and 23a correspond to a heater. This heater is used to heat the gas sensor to an activation temperature, thereby increasing the oxygen ion conductivity of each solid electrolyte layer for stable operation.

The insulating layers 23a to 23e are formed mainly of alumina, and the first diffusion resistor element 8a and the second diffusion resistor element 8b are formed of a porous material such as alumina. The heating resistor element 21 is formed of, for example, platinum. The heat generating portion of the heating resistor element 21 may be formed into a meandering pattern.

The first pumping cell 2 pumps out oxygen from the exhaust gas (the gas under measurement) introduced into the first measurement chamber S1 and pumps oxygen into the exhaust gas. The first pumping cell 2 includes a first solid electrolyte layer 2a formed mainly of zirconia having oxygen ion conductivity, and an inner first pumping electrode 2b and an outer (counter) first pumping electrode 2c disposed to sandwich the first solid electrolyte layer 2a. The inner first pumping electrode 2b faces the first measurement chamber S1. Each of the inner first pumping electrode 2b and the outer first pumping electrode 2c is formed mainly of platinum, and the surface of the inner first pumping electrode 2b is covered with a protection layer 11 formed of a porous material.

A portion of the insulating layer 23e corresponding to the upper surface of the outer first pumping electrode 2c is removed to form a space, and a porous material 13 fills the space. The porous material 13 establishes communication between the outer first pumping electrode 2c and the outside, thereby allowing a gas (oxygen) to enter and leave.

Notably, the oxygen concentration in the exhaust gas (the gas under measurement) can be determined based on a first pumping current Ip1 flowing through the first pumping cell (an example of the oxygen detection section) 2. As described below, the oxygen concentration in the exhaust gas obtained from the first pumping current Ip1 is used for detection of the ammonia concentration in the exhaust gas.

The oxygen concentration detection cell 6 includes a third solid electrolyte layer 6a formed mainly of zirconia, and a detection electrode 6b and a reference electrode 6c disposed to sandwich the third solid electrolyte layer 6a. The detection electrode 6b faces the first measurement chamber S1 in a region downstream of the inner first pumping electrode 2b. Each of the detection electrode 6b and the reference electrode 6c is formed mainly of platinum.

Notably, the insulating layer 23c is cut out to form a space in which the reference electrode 6c in contact with the third solid electrolyte layer 6a is disposed. A porous material is charged into the cut out portion (the space), whereby a reference oxygen chamber 15 is formed. When a constant weak current is supplied to the oxygen concentration detection cell 6 beforehand by using an Icp supply circuit 54, the oxygen concentration detection cell 6 supplies oxygen from the first measurement chamber S1 into the reference oxygen chamber 15. The oxygen within the reference oxygen chamber 15 serves as an oxygen reference.

The second pumping cell 4 includes a second solid electrolyte layer 4a formed mainly of zirconia, an inner second pumping electrode 4b disposed on a surface region of the second solid electrolyte layer 4a facing the second measurement chamber S2, and a second pumping counter electrode 4c serving as a counter electrode. Each of the inner second pumping electrode 4b and the second pumping counter electrode 4c is mainly formed of platinum. Notably, the second pumping counter electrode 4c is disposed in a cut out portion (space) of the insulating layer 23c located on the second solid electrolyte layer 4a. The second pumping counter electrode 4c is opposed to the reference electrode 6c and faces the reference oxygen chamber 15.

As shown in FIG. 2, the inner first pumping electrode 2b, the detection electrode 6b, and the inner second pumping electrode 4b are connected to a line maintained at a reference potential. Notably, constituent elements (for example, the first pumping cell 2, the oxygen concentration detection cell 6, the second pumping cell 4, etc.) of the NOx sensor section 30A, excluding the heating resistor element 21 and the insulating layers 23b and 23a, constitute an NOx detection section.

Figure 3:
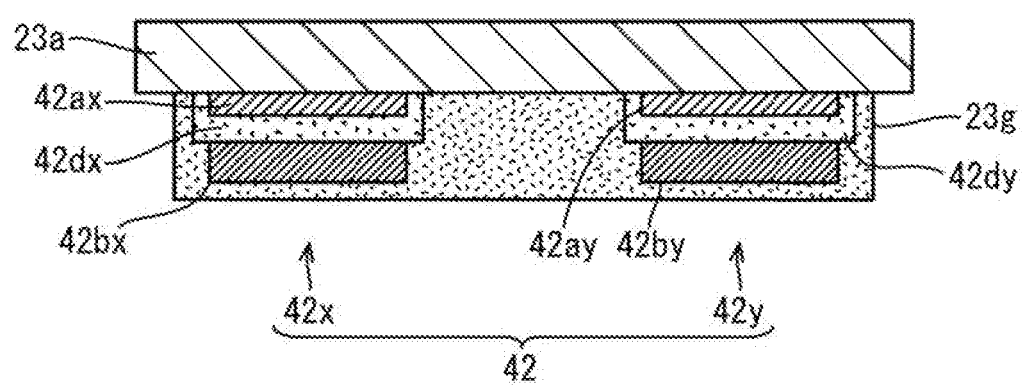
FIG. 3 is a sectional view showing the structure of an ammonia sensor section.

Next, the ammonia sensor section 42 will be described. The ammonia sensor section 42 includes two mixed-potential-type ammonia sensor sections (a first ammonia sensor section 42x and a second ammonia sensor section 42y). FIG. 3 is a cross sectional view showing the structure of the ammonia sensor section 42. As shown in FIG. 3, the multi-gas sensor element 100A includes, as ammonia sensor sections, the first ammonia sensor section 42x and the second ammonia sensor section 42y which are spaced apart from each other in the widthwise direction. Notably, each of the first ammonia sensor section 42x and the second ammonia sensor section 42y includes a mixed-potential cell.

The first ammonia sensor section 42x and the second ammonia sensor section 42y are formed on the insulating layer 23a, which forms the outer surface (lower surface) of the NOx sensor section 30A. In the first ammonia sensor section 42x, a first reference electrode 42ax is formed on the insulating layer 23a, and a first solid electrolyte layer 42dx is formed to cover the lower and side surfaces of the first reference electrode 42ax. Moreover, a first detection electrode 42bx is formed on the surface of the first solid electrolyte layer 42dx. The ammonia concentration in the gas under measurement is detected from a change in the electromotive force between the first reference electrode 42ax and the first detection electrode 42bx. Similarly, in the second ammonia sensor section 42y, a second reference electrode 42ay is formed on the insulating layer 23a, and a second solid electrolyte layer 42dy is formed to cover the lower and side surfaces of the second reference electrode 42ay. Moreover, a second detection electrode 42by is formed on the surface of the second solid electrolyte layer 42dy. The ammonia concentration in the gas under measurement is detected from a change in the electromotive force between the second reference electrode 42ay and the second detection electrode 42by.

In the present embodiment, the NOx detection section and the ammonia sensor section 42 (the first ammonia sensor section 42x and the second ammonia sensor section 42y) are disposed to sandwich the heater (the heating resistor element 21, the insulating layer 23b, and the insulating layer 23a) in the stacking direction. Therefore, each of the NOx detection section and the two ammonia sensor sections 42x and 42y is located adjacent to the heater (is at approximately the same distance from the heater). As a result, temperature control for the two ammonia sensor sections 42x and 42y can be performed more accurately.

The first ammonia sensor section 42x and the second ammonia sensor section 42y are integrally covered with a protection layer 23g formed of a porous material. The protection layer 23g prevents adhesion of poisoning substances to the first detection electrode 42bx and the second detection electrode 42by, and adjusts the diffusion rate of the gas under measurement flowing into the first ammonia sensor section 42x and the second ammonia sensor section 42y from the outside. The protection layer 23g is formed through use of at least one type of material selected from a group consisting of alumina (aluminum oxide), spinel ($MgAl_2O_4$), silica alumina, and mullite. The rate of diffusion of the gas under measurement through the protection layer 23g is adjusted by appropriately setting various conditions such as the thickness, particle size, particle size distribution, porosity, material blending ratio, etc., of the protection layer 23g.

Notably, in other embodiments, the protection layer 23g may be omitted to expose the first ammonia sensor section 42x, the second ammonia sensor section 42y, etc., or separate protection layers may be individually provided for the first ammonia sensor section 42x and the second ammonia sensor section 42y.

The first detection electrode 42bx and the second detection electrode 42by may be formed from a material containing Au as a main component (for example, 70 mass % or more). The first reference electrode 42ax and the second reference electrode 42ay may be formed from a material containing Pt only or containing Pt as a main component (for example, 70 mass % or more). Combustion of ammonia gas does not easily occur on the surfaces of the first detection electrode 42bx and the second detection electrode 42by. Ammonia passes through the detection electrode 42bx (42by) and reacts with oxygen ions at the interface between the detection electrode 42bx (42by) and the reference electrode 42ax (42ay) (electrode reaction), whereby the concentration of ammonia is detected. Notably, the details of a specific process for detecting the ammonia concentration described below.

Notably, in the present embodiment, the impedance of the oxygen concentration detection cell 6 is measured, and the heater (the heating resistor element 21) is activated for heating on the basis of the measured impedance. Therefore, the temperature of the multi-gas sensor element 100A is maintained at a most stable value (temperature estimable value) in the vicinity of the oxygen concentration detection cell 6. Since the first ammonia sensor section 42x and the second ammonia sensor section 42y are disposed in the vicinity of the oxygen concentration detection cell 6, the two ammonia sensor sections 42x and 42y are maintained at a stable temperature.

Next, referring back to FIG. 2, an example of the configuration of the gas sensor control apparatus 300 will be described. The gas sensor control apparatus 300 includes a (analog) control circuit 59 and a microcomputer (sensor control unit, SCU) 60 disposed on a circuit board. The microcomputer 60, which controls the entirety of the gas sensor control apparatus 300, includes a CPU (central processing unit) 61, a RAM 62, a ROM 63, a signal input/output section 64, an A/D converter 65, an unillustrated clock, etc. In the microcomputer 60, programs stored in the ROM 63, etc., in advance are executed by the CPU 61.

The control circuit 59 includes a reference voltage comparison circuit 51, an Ip1 drive circuit 52, a Vs detection circuit 53, an Icp supply circuit 54, an Ip2 detection circuit 55, a Vp2 application circuit 56, a heater drive circuit 57, a first electromotive force detection circuit 58a, and a second electromotive force detection circuit 58b.

The control circuit 59 controls the NOx sensor section 30A, detects the first and second pumping currents Ip1 and Ip2 flowing through the NOx sensor section 30A, and outputs the detected first and second pumping currents Ip1 and Ip2 to the microcomputer 60.

The first electromotive force detection circuit 58a detects the ammonia concentration output (electromotive force) between the electrodes of the first ammonia sensor section 42x, and outputs the detected ammonia concentration output to the microcomputer 60. Similarly, the second electromotive force detection circuit 58b detects the ammonia concentration output (electromotive force) between the electrodes of the second ammonia sensor section 42y, and outputs the detected ammonia concentration output to the microcomputer 60.

The outer first pumping electrode 2c of the NOx sensor section 30A is connected to the Ip1 drive circuit 52, and the reference electrode 6c is connected to the Vs detection circuit 53 and the Icp supply circuit 54. The second pumping counter electrode 4c is connected to the Ip2 detection circuit 55 and the Vp2 application circuit 56. The heater drive circuit 57 is connected to the heater (specifically, the heating resistor element 21).

The pair of electrodes 42ax and 42bx of the first ammonia sensor section 42x are connected to the first electromotive force detection circuit 58a. Similarly, the pair of electrodes 42ay and 42by of the second ammonia sensor section 42y are connected to the second electromotive force detection circuit 58b.

The circuits 51 to 57 have the following functions. The Ip1 drive circuit 52 supplies the first pumping current Ip1 flowing between the inner first pumping electrode 2b and the outer first pumping electrode 2c and detects the first pumping current Ip1 at that time. The Vs detection circuit 53 detects the voltage Vs between the detection electrode 6b and the reference electrode 6c, and outputs the detected voltage to the reference voltage comparison circuit 51.

The reference voltage comparison circuit 51 compares a reference voltage (for example, 425 mV) and the output (the voltage Vs) of the Vs detection circuit 53, and outputs the comparison result to the Ip1 drive circuit 52. The Ip1 drive circuit 52 controls the flow direction and magnitude of the current Ip1 such that the voltage Vs becomes equal to the above-described reference voltage, thereby adjusting the oxygen concentration within the first measurement chamber S1 to a predetermined concentration at which NOx does not decompose.

The Icp supply circuit 54 supplies a very weak current Icp which flows between the detection electrode 6b and the reference electrode 6c so as to supply oxygen from the first measurement chamber S1 into the reference oxygen chamber 15, thereby exposing the reference electrode 6c to oxygen of a predetermined concentration serving as a reference.

The Vp2 application circuit 56 applies a constant voltage Vp2 (for example, 450 mV) between the inner second pumping electrode 4b and the second pumping counter electrode 4c. The constant voltage Vp2 is high enough to decompose the NOx gas contained in the gas under measurement to oxygen and $N_2$ gas. As a result, NOx is decomposed to nitrogen and oxygen.

The Ip2 detection circuit 55 detects the second pumping current Ip2 flowing through the second pumping cell 4 when oxygen produced as a result of decomposition of NOx is pumped out from the second measurement chamber S2 toward the second pumping counter electrode 4c through the second solid electrolyte layer 4a.

The Ip1 drive circuit 52 outputs the value of the detected first pumping current Ip1 to the A/D converter 65. The Ip2 detection circuit 55 outputs the value of the detected second pumping current Ip2 to the A/D converter 65. The A/D converter 65 converts these values to digital values and outputs the digital values to the CPU 61 via the signal input/output section 64.

Next, an example of control performed through use of the control circuit 59 provided in the gas sensor control apparatus 300 will be described. When an engine is started and electric power is supplied from an external power source, the heater is activated by the heater drive circuit 57, whereby the first pumping cell 2, the oxygen concentration detection cell 6, and the second pumping cell 4 are heated to their activation temperatures. The Icp supply circuit 54 supplies the weak current Icp which flows between the detection electrode 6b and the reference electrode 6c so as to supply oxygen from the first measurement chamber S1 into the reference oxygen chamber 15, so that the oxygen within the reference oxygen chamber 15 serves as a reference. When the NOx sensor section 30A is heated to an appropriate temperature by the heater, the first ammonia sensor section 42x and the second ammonia sensor section 42y on the NOx sensor section 30A are also heated to a desired temperature.

After the cells have been heated to their activation temperatures, the first pumping cell 2 pumps out oxygen contained in the exhaust gas flowing into the first measurement chamber S1. The pumped out oxygen flows from the inner first pumping electrode 2b toward the outer first pumping electrode 2c. At that time, the oxygen concentration within the first measurement chamber S1 corresponds to the voltage (inter-electrode voltage) Vs between the electrodes of the oxygen concentration detection cell 6. Therefore, the Ip1 drive circuit 52 controls the first pumping current Ip1 flowing through the first pumping cell 2 such that the inter-electrode voltage Vs becomes equal to the above-described reference voltage (for example, 425 mV). In this manner, the oxygen concentration within the first measurement chamber S1 is adjusted to a concentration at which NOx does not decompose. Notably, the oxygen concentration in the exhaust gas flowing into the first measurement chamber S1 is determined based on the first pumping current Ip1 detected by the Ip1 drive circuit 52, and the oxygen concentration is utilized for detecting the concentration of ammonia, described below.

The gas under measurement whose oxygen concentration has been adjusted flows further toward the second measurement chamber S2. The Vp2 application circuit 56 applies the constant voltage Vp2 between the electrodes of the second pumping cell 4 as an inter-electrode voltage. The constant voltage Vp2 is high enough to decompose the NOx gas contained in the gas under measurement to oxygen and $N_2$ gas (a voltage higher than the value of the control voltage of the oxygen concentration detection cell 6, for example, 450 mV). As a result, NOx is decomposed to nitrogen and oxygen. The second pumping current Ip2 flows through the second pumping cell 4 so that oxygen produced as a result of decomposition of NOx is pumped out from the second measurement chamber S2. At that time, the NOx concentration in the gas under measurement can be detected by detecting the second pumping current Ip2.

As described below, the ammonia concentration in the gas under measurement can be determined by detecting the ammonia concentration output (electromotive force) between the pair of electrodes 42ax and 42bx by the first electromotive force detection circuit 58a. Also, the ammonia concentration in the gas under measurement can be determined by detecting the ammonia concentration output (electromotive force) between the pair of electrodes 42ay and 42by by the second electromotive force detection circuit 58b.

Next, processes for calculating various gas concentrations (in particular, ammonia concentration) performed by the microcomputer (SCU) 60 of the gas sensor control apparatus 300 described below.

Notably, since the ammonia sensor section 42 detects not only ammonia but also $NO_2$, if $NO_2$ gas is contained in the gas under measurement in addition to ammonia, the accuracy in detecting ammonia may be lowered. In view of the above, the concentration of ammonia and the concentration of $NO_2$ are calculated individually by utilizing, as the ammonia sensor section 42, two ammonia sensor sections 42 which differ from each other in terms of the ratio between the sensitivity to ammonia and the sensitivity to NOx.

For example, the sensor output of each ammonia sensor section 42 is represented by F(x, y, D), where x: ammonia concentration, y: $NO_2$ gas concentration, and D: $O_2$ concentration. When two ammonia sensor sections having different sensitivity ratios are used, two expressions $F_1$(mx, ny, D) and $F_2$(sx, ty, D) are obtained, where m, n, s, and t are coefficients). Since $F_1$, $F_2$, and D can be obtained from the sensor outputs, two unknown quantities (x, y) can be obtained from the two expressions.

In the present specification, detection of ammonia by the ammonia sensor section 42 and calculation of ammonia concentration will be described in detail. Notably, a detailed description of detection of $NO_2$ by the ammonia sensor section 42 and a process for calculating the concentration of $NO_2$ is omitted.

Electromotive force is generated between the first reference electrode 42ax and the first detection electrode 42bx of the first ammonia sensor section (an example of the ammonia detection section) 42x in accordance with the concentration of ammonia contained in the exhaust gas (the gas under measurement). The first electromotive force detection circuit 58a detects the electromotive force between the first reference electrode 42ax and the first detection electrode 42bx as a first ammonia electromotive force EMF1.

Similarly, an electromotive force is generated between the second reference electrode 42ay and the second detection electrode 42by of the second ammonia sensor section (an example of the ammonia detection section) 42y in accordance with the concentration of ammonia contained in the gas under measurement. The second electromotive force detection circuit 58b detects the electromotive force between the second reference electrode 42ay and the second detection electrode 42by as a second ammonia electromotive force EMF2.

For example, various types of data described below (relational expressions, etc.) are stored in the ROM 63 of the microcomputer 60. The CPU 61 reads out the various types of data from the ROM 63 and performs various computation processes while using the value of the first pumping current Ip1, the value of the second pumping current Ip2, the first ammonia electromotive force EMF1, and the second ammonia electromotive force EMF2.

The ROM 63 stores therein a "first ammonia electromotive force & $O_2$ concentration output–ammonia concentration output relational expression," a "second ammonia electromotive force & $O_2$ concentration output–ammonia concentration output relational expression," a "first pumping current Ip1–$O_2$ concentration output relational expression," a "second pumping current Ip2–NOx concentration output relational expression," etc.

The "first ammonia electromotive force & $O_2$ concentration output–ammonia concentration output relational expression" represents the relation among the first ammonia electromotive force EMF1 output from the first ammonia sensor section 42x, $O_2$ concentration output derived from the "first pumping current Ip1–$O_2$ concentration output relational expression" described below, and ammonia concentration output (first ammonia concentration) regarding the ammonia concentration of the gas under measurement determined without mitigating (without consideration of) the influence of the pressure of the gas under measurement.

The "second ammonia electromotive force & $O_2$ concentration output–ammonia concentration output relational expression" represents the relation among the second ammonia electromotive force EMF2 output from the second ammonia sensor section 42y, the $O_2$ concentration output derived from the "first pumping current Ip1–$O_2$ concentration output relational expression" described below, and the ammonia concentration output (first ammonia concentration) regarding the ammonia concentration of the gas under measurement determined without mitigating (without consideration of) the influence of the pressure of the gas under measurement.

The "first pumping current Ip1–$O_2$ concentration output relational expression" represents the relation between the first pumping current Ip1 and the $O_2$ concentration of the gas under measurement.

The "second pumping current Ip2–NOx concentration output relational expression" represents the relation between the second pumping current Ip2 and the NOx concentration of the gas under measurement.

Notably, the various types of data may be set as predetermined relational expressions as described above or may be set in other forms so long as the various gas concentrations can be calculated from the outputs of the sensor. For example, the various types of data may be set as data tables. Alternatively, the various types of data may be values (in the form of relational expressions, tables, etc.) obtained beforehand through use of a gas model whose gas concentrations are known.

Next, an ammonia concentration detection process for detecting the concentration of ammonia (an example of the second ammonia concentration) executed by the CPU (an example of the control section) 61 of the microcomputer 60 will be described. Herein, there will be described a process for detecting the ammonia concentration in the gas under measurement by utilizing the first ammonia electromotive force EMF1 detected by the first ammonia sensor section 42x, the first pumping current Ip1, etc.

Figure 4:
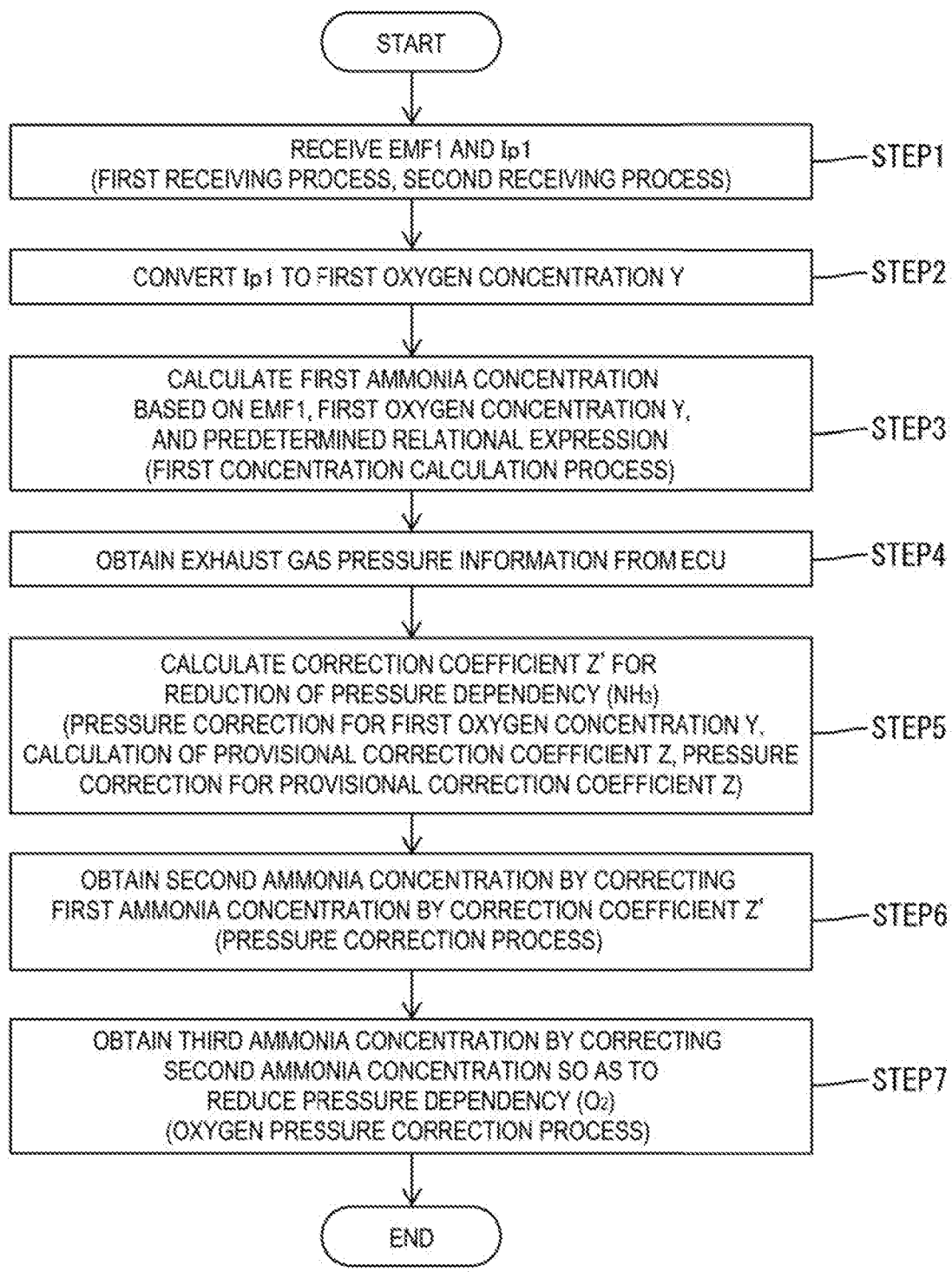
FIG. 4 is a flowchart showing the details of an ammonia concentration detection process.

FIG. 4 is a flowchart showing the details of the ammonia concentration detection process. First, in the multi-gas sensor apparatus 400 (see FIG. 2), the first ammonia electromotive force EMF1 (an example of the first detection result) output from the first ammonia sensor section 42x is detected via the first electromotive force detection circuit 58a, and information representing the first ammonia electromotive force EMF1 is received by the microcomputer 60 of the gas sensor control apparatus 300 (first receiving process, STEP 1 of FIG. 4).

Meanwhile, the first pumping current Ip1 output from the first pumping cell 2 (an example of the second detection result) is detected via the Ip1 drive circuit 52, and information representing the first pumping current Ip1 is received by the microcomputer 60 (second receiving process, STEP 1 of FIG. 4). Notably, for example, the first pumping current Ip1 detected at the same timing (at the same point in time) as the timing of detection of the first ammonia electromotive force is used.

When the information representing the first pumping current Ip1 is input to the CPU 61 of the microcomputer 60, the CPU 61 retrieves the "first pumping current Ip1–$O_2$ concentration output relational expression" from the ROM 63 and converts the first pumping current Ip to a first oxygen concentration Y (an example of the second detection result) by using the relational expression (output conversion process, STEP 2 of FIG. 4).

Next, the CPU 61 retrieves the "first ammonia electromotive force & $O_2$ concentration output–ammonia concentration output relational expression" from the ROM 63 and calculates the first ammonia concentration by utilizing the relational expression, the first ammonia electromotive force EMF1, and the first oxygen concentration Y (first concentration calculation process, STEP 3 of FIG. 4). The first ammonia concentration is a provisional ammonia concentration determined without mitigating (without consideration of) the influence of the pressure of the gas under measurement.

Figure 5:
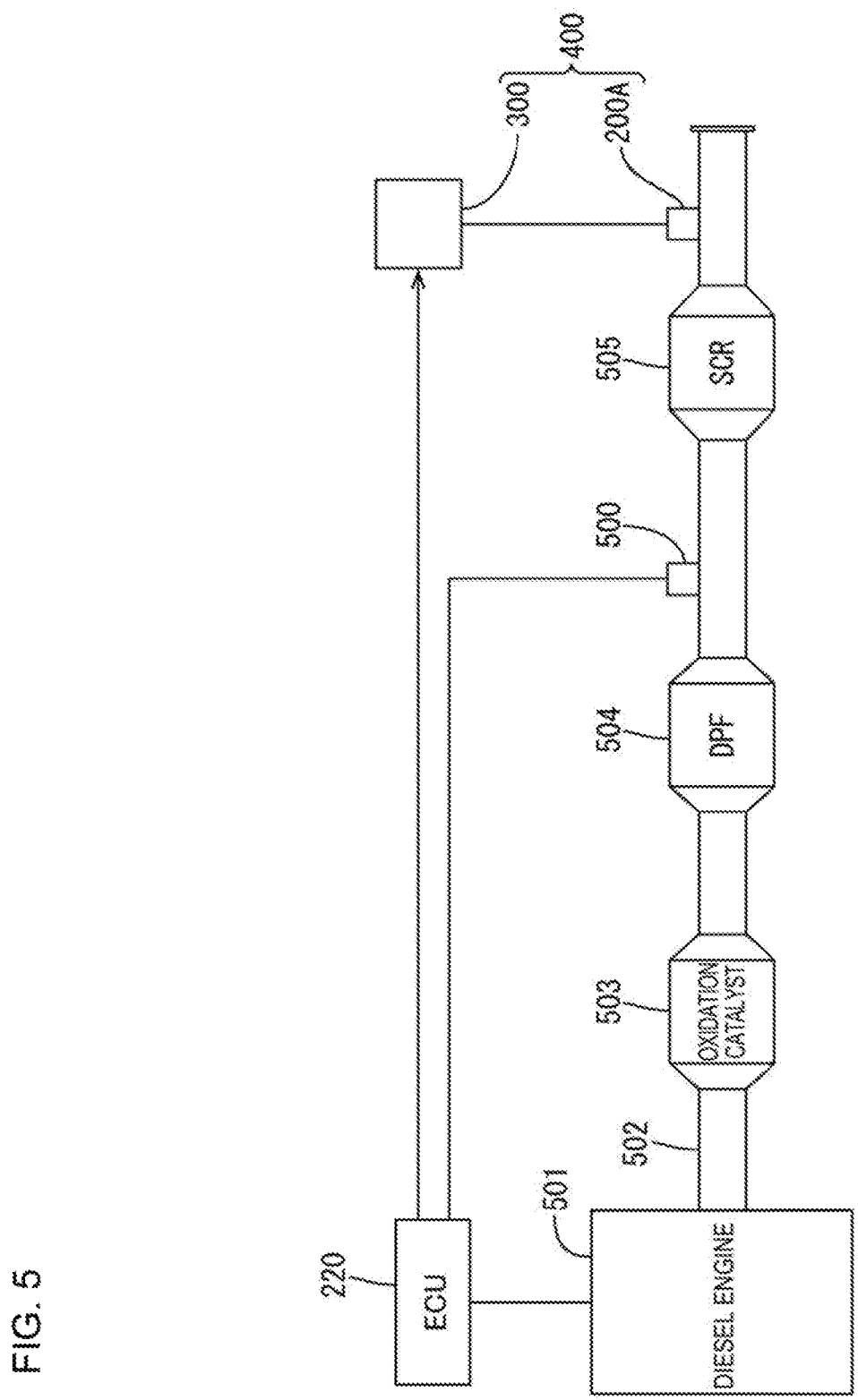
FIG. 5 is an explanatory diagram showing the location where a pressure sensor for detecting the pressure of a gas under measurement is disposed.

Subsequently, the CPU 61 obtains information representing the pressure of the exhaust gas (the gas under measurement) from the ECU 220, which is an external device (pressure information obtaining process, STEP 4 of FIG. 4). Here, a pressure sensor 500 for detecting the pressure of the gas under measurement, etc., will be described with reference to FIG. 5. FIG. 5 is an explanatory diagram showing the location where a pressure sensor 500 for detecting the pressure of the gas under measurement is disposed. In FIG. 5, an oxidation catalyst 503, a DPF (diesel particulate filter) 504, and an SCR (selective catalytic reduction) catalyst 505 are provided midway in an exhaust pipe 502 of a diesel engine (internal combustion engine) 501 such that these components are arranged in this order from the upstream side. The pressure sensor 500 is mounted on the exhaust pipe 502 at a location between the DPF 504 and the SCR catalyst 505 and detects the pressure of the exhaust gas (the gas under measurement) flowing through the exhaust pipe 502. Notably, the multi-gas sensor 200A of the multi-gas sensor apparatus 400 is mounted on the exhaust pipe 502 at a location adjacent to and downstream of the SCR catalyst 505.

The pressure (measured value) detected by the pressure sensor 500 is stored in a storage device (ROM such as EPROM or EEPROM) provided in the ECU 220. The CPU 61 of the gas sensor control apparatus 300 (the microcomputer 60) executes a process for obtaining, from the ECU 220, information representing the pressure detected by the pressure sensor 500. Notably, the pressure information obtained by the microcomputer 60 represents the absolute pressure of the gas under measurement (101.325+P), where P is the measurement value output from the pressure sensor 500. The pressure information used may be information representing the pressure detected by the pressure sensor 500 at the same timing (at the same point in time) as the timing of detection of the first ammonia electromotive force EMF1 or information representing the pressure detected by the pressure sensor 500 after elapse of a predetermined time after the detection of the first ammonia electromotive force EMF1.

Next, as shown in FIG. 4, for the purpose of mitigating the influence of the pressure of the gas under measurement, the CPU 61 executes a process for calculating a correction coefficient Z' for correcting the first ammonia concentration (correction coefficient calculation process, STEP 5 of FIG. 4). Here, the first oxygen concentration Y is first corrected based on the measured pressure, whereby a second oxygen concentration Y' is obtained. Specifically, the second oxygen concentration Y' is calculated, for example, based on the first oxygen concentration Y and a relational expression (1) shown below.

$$Y'=Y*(101.325+P+k)/(101.325+P)*101.325/(101.325+k) \quad \text{Relational expression (1)}$$

(P in the above-described expression represents the measured pressure of the gas under measurement, and k is a pressure correction coefficient.)

Subsequently, a provisional correction coefficient Z is calculated based on the second oxygen concentration Y' and a relational expression (2) shown below.

$$Z=a*Y'^2+b*Y'+c \quad \text{Relational expression (2)}$$

(a, b, and c in the above-described expression are coefficients.)

When the provisional correction coefficient Z is corrected based on the measured pressure, a correction coefficient Z' for correcting the first ammonia concentration is obtained. Specifically, the correction coefficient Z' for correcting the first ammonia concentration is obtained, for example, based on the provisional correction coefficient Z and a relational expression (3) shown below.

$$Z'=Z*((101.325+P+k')/(101.325+P)*101.325/(101.325+k'))*(a*\ln(Y')+b) \quad \text{Relational expression (3)}$$

(P in the above-described expression represents the measured pressure of the gas under measurement, k' is a pressure correction coefficient, and a and b are coefficients.)

Next, as shown in STEP 6 of FIG. 4, the CPU 61 executes a process for obtaining the second ammonia concentration of the gas under measurement. This is done by correcting the first ammonia concentration through utilizing the correction coefficient Z' based on the pressure information representing the pressure of the gas under measurement (pressure correction process). Here, the second ammonia concentration that is less influenced by the pressure of the gas under measurement is obtained by multiplying the first ammonia concentration by the correction coefficient Z'. In this manner, the second ammonia concentration that is less influenced by the pressure of the gas under measurement is simply obtained.

Notably, in the case of the present embodiment, as shown in FIG. 2, the first pumping cell 2 pumps oxygen out of and into the gas under measurement (exhaust gas) introduced from the outside (the interior of the exhaust pipe) into the first measurement chamber S1 through the porous protection layer 9 and the first diffusion resistor element 8a. Therefore, the first pumping current Ip1 output from the first pumping cell 2 is influenced by the pressure of the gas under measurement. In view of the above, in the present embodiment, as shown in STEP 7 of FIG. 4, a process for correcting the second ammonia concentration, for example, based on the above-described pressure information representing the pressure of the gas under measurement (oxygen pressure correction process) is executed in order to mitigate the influence of the pressure on oxygen concentration. As a result of execution of this process, the third ammonia concentration of the gas under measurement is obtained while the influence of the pressure of the gas under measurement on oxygen concentration is mitigated.

In the above-described manner, the ammonia concentrations (the second ammonia concentration and the third ammonia concentration) in a state in which the influence of the pressure of the gas under measurement on ammonia concentration has been mitigated are obtained by utilizing the first ammonia electromotive force EMF1 detected by the first ammonia sensor section 42x (an example of the first detection result), the first pumping current Ip1 (an example of the second detection result), the pressure information representing the pressure of the gas under measurement, etc. Notably, the third ammonia concentration is the ammonia concentration in the gas under measurement determined by mitigating not only the influence of the pressure of the gas under measurement on ammonia concentration, but also the influence of the pressure of the gas under measurement on oxygen concentration.

In the second ammonia sensor section 42y as well, similarly, the second ammonia concentration and the third ammonia concentration are obtained by utilizing the second ammonia electromotive force EMF2 (an example of the first detection result), the first pumping current Ip1 (an example of the second detection result), the pressure information representing the pressure of the gas under measurement, etc. The second ammonia concentration is the ammonia concentration in the gas under measurement determined by mitigating the influence of the pressure of the gas under measurement on ammonia concentration. The third ammonia concentration is the ammonia concentration in the gas under measurement determined by mitigating not only the influence of the pressure of the gas under measurement on ammonia concentration but also the influence of the pressure of the gas under measurement on oxygen concentration.

Notably, the $NO_2$ gas concentration, etc. are obtained by using the respective third ammonia concentrations obtained from the first ammonia sensor section 42x and the second ammonia sensor section 42y, etc.

As described above, according to the multi-gas sensor apparatus 400 (the gas sensor control apparatus 300) of the present embodiment, the accuracy in measuring the ammonia concentration can be improved by mitigating the influence of the pressure of the gas under measurement on ammonia concentration. In particular, in the case of the present embodiment, the accuracy in measuring the ammonia concentration can be improved further by mitigating the influence of the pressure of the gas under measurement on oxygen concentration.

Ammonia Detection Test 1

An ammonia detection test described below was carried out using the multi-gas sensor apparatus 400 of the first embodiment. A predetermined exhaust pipe was prepared, and the multi-gas sensor apparatus 400 was disposed midway in the exhaust pipe. In a state in which a gas under measurement (air) containing ammonia of a predetermined concentration was supplied to the exhaust pipe, the pressure of the gas under measurement was changed to different pressures, thereby producing different pressure conditions. The ammonia concentration was detected by the multi-gas sensor apparatus 400 in each of the pressure conditions. For the test, the multi-gas sensor apparatus 400 was set to detect the ammonia concentration not subjected to the above-described pressure correction process and oxygen correction process (the first ammonia concentration), and the ammonia concentration subjected to the above-described pressure correction process and oxygen correction process (the second ammonia concentration).

Figure 6:
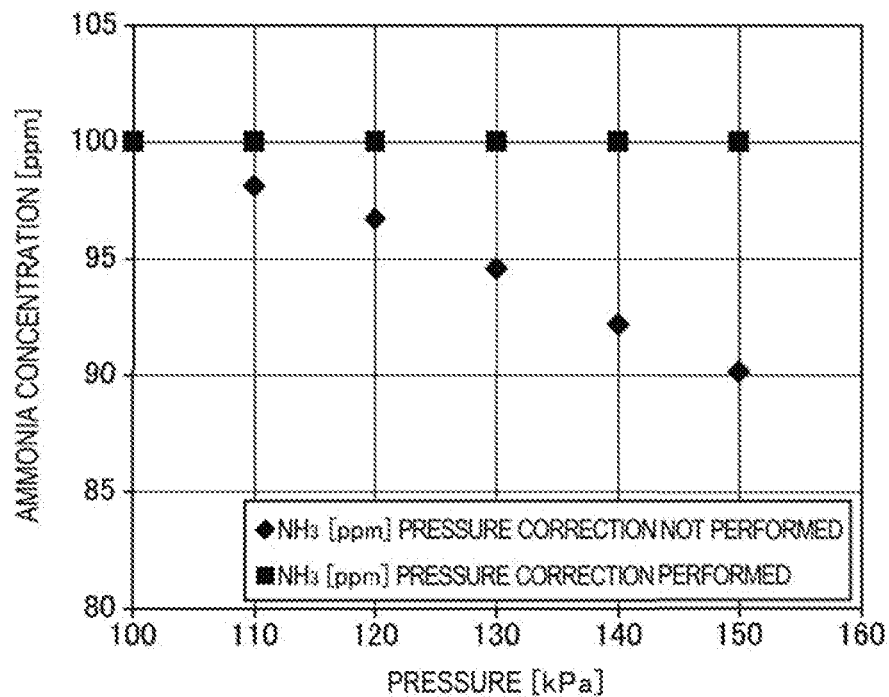
FIG. 6 is a graph showing the relation between the pressure of the gas under measurement and ammonia concentration influenced by the pressure of the gas under measurement.

FIG. 6 is a graph showing the relation between the pressure of the gas under measurement and the ammonia concentration influenced by the pressure of the gas under measurement. In the graph of FIG. 6, the horizontal axis represents the pressure (kPa), and the vertical axis represents the ammonia concentration (ppm). As shown in FIG. 6, it was confirmed that the value of the ammonia concentration not subjected to the above-described pressure correction process and oxygen correction process (the first ammonia concentration) is smaller than the real value (set value), and the difference between the value of ammonia concentration and the real value increases as the pressure of the gas under measurement increases.

Oxygen Concentration Detection Test

An oxygen concentration detection test described below was carried out using the multi-gas sensor apparatus 400 of the first embodiment. An exhaust pipe similar to that used in the above-described ammonia detection test 1 was prepared, and the multi-gas sensor apparatus 400 was disposed midway in the exhaust pipe. In a state in which a gas under measurement (air) containing oxygen of a predetermined concentration was supplied to the exhaust pipe, the pressure of the gas under measurement was changed to different pressures, thereby producing different pressure conditions. The oxygen concentration was detected by the multi-gas sensor apparatus 400 in each of the pressure conditions. For the test, the multi-gas sensor apparatus 400 was set to detect the oxygen concentration obtained by converting the first pumping current Ip1 (the first oxygen concentration Y) and the second oxygen concentration Y' obtained by correcting the first oxygen concentration Y on the basis of the pressure.

Figure 7:
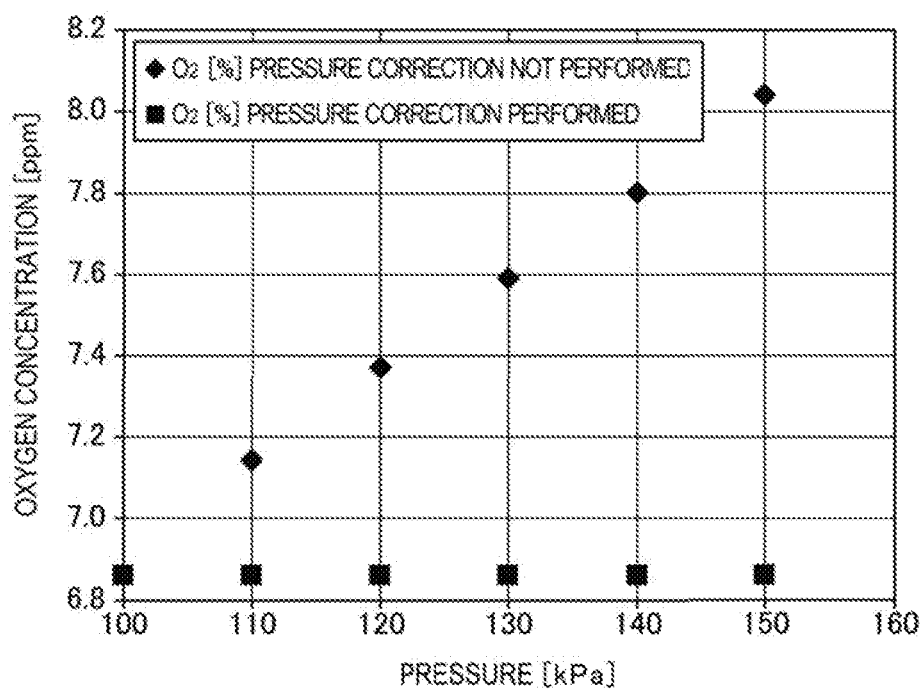
FIG. 7 is a graph showing the relation between the pressure of the gas under measurement and oxygen concentration influenced by the pressure of the gas under measurement.

FIG. 7 is a graph showing the relation between the pressure of the gas under measurement and the oxygen concentration influenced by the pressure of the gas under measurement. In the graph of FIG. 7, the horizontal axis represents the pressure (kPa), and the vertical axis represents the oxygen concentration (ppm). As shown in FIG. 7, it was confirmed that the value of the first oxygen concentration Y not subjected to the pressure correction is larger than the real value (set value), and the difference between the value of the first oxygen concentration and the real value increases as the pressure of the gas under measurement increases.

Ammonia Detection Test 2

An ammonia detection test described below was carried out using the multi-gas sensor apparatus 400 of the first embodiment. A predetermined exhaust pipe was prepared, and the multi-gas sensor apparatus 400 was disposed midway in the exhaust pipe. In a state in which a gas under measurement (air) containing ammonia of a predetermined concentration was supplied to the exhaust pipe, the pressure of the gas under measurement was changed to different pressures, thereby producing different pressure conditions. The ammonia concentration was detected by the multi-gas sensor apparatus 400 in each of the pressure conditions. For the test, the multi-gas sensor apparatus 400 was set to detect the ammonia concentration subjected only to the above-described pressure correction process and not subjected to the oxygen correction process (the second ammonia concentration), and to detect the ammonia concentration subjected to the above-described pressure correction process and oxygen correction process (the third ammonia concentration). Notably, the above-described pressure conditions of the gas under measurement were utilized as the pressure information representing the pressure of the gas under measurement.

Figure 8:
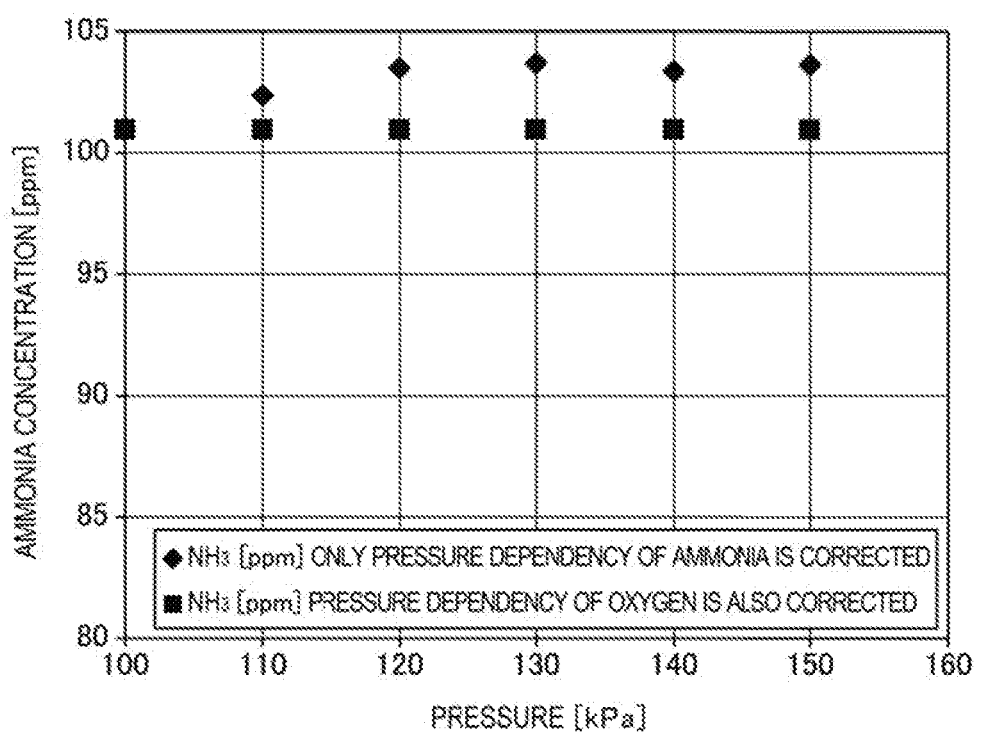
FIG. 8 is a graph showing the relation between the pressure of the gas under measurement and ammonia concentration determined in a state in which only the influence of the pressure of the gas under measurement on ammonia concentration has been lessened.

FIG. 8 is a graph showing the relation between the pressure of the gas under measurement and the ammonia concentration determined by mitigating only the influence of the pressure of the gas under measurement on ammonia concentration. In the graph of FIG. 8, the horizontal axis represents the pressure (kPa), and the vertical axis represents the ammonia concentration (ppm). Errors of about several ppm were observed between the real value (set value) and the value of the second ammonia concentration subjected only to the pressure correction process and not subjected to the oxygen correction process due to the influence of the pressure of the gas under measurement on oxygen concentration.

Embodiment 2

Figure 9:
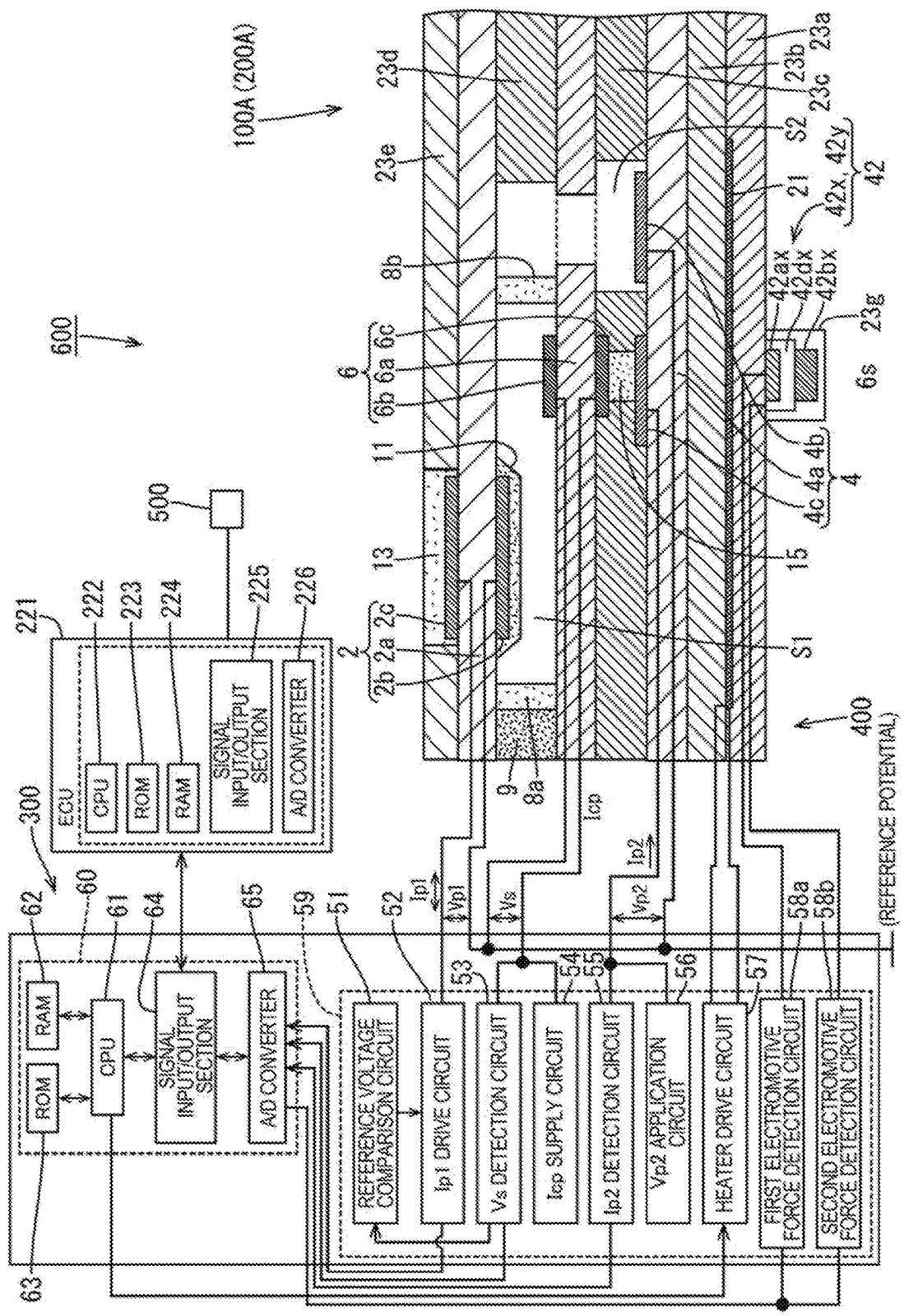
FIG. 9 is an explanatory diagram schematically showing the configuration of an internal combustion engine control system according to a second embodiment.

Next, a second embodiment of the present invention will be described with reference to FIGS. 9 and 10. In the present embodiment, an internal combustion engine control system 600 which is provided for an internal combustion engine (for example, a diesel engine) of an automobile and controls the operation state of the internal combustion engine will be described. FIG. 9 is an explanatory diagram schematically showing the configuration of the internal combustion engine control system 600 according to the second embodiment. The internal combustion engine control system 600 includes a multi-gas sensor apparatus 400 as a sensor for detecting NOx and ammonia contained in the exhaust gas (the gas under measurement) discharged from the internal combustion engine. In addition to the multi-gas sensor apparatus 400, the internal combustion engine control system 600 includes an ECU 221 serving as an internal combustion engine control apparatus, and a pressure sensor 500 for detecting the pressure of the exhaust gas.

The basic structure of the multi-gas sensor apparatus 400 is the same as that of the above-described first embodiment. Further, reference numerals in FIG. 9 which are the same as in FIG. 5 define the same structures. However, in the present embodiment, the process for detecting the ammonia concentration in the exhaust gas is not performed in the gas sensor control apparatus 300 provided in the multi-gas sensor apparatus 400, and that process is performed in the ECU (internal combustion engine control apparatus) 221 provided in the internal combustion engine control system 600. The ECU 221 includes a CPU (an example of the control section) 222, a ROM 223, a RAM 224, a signal input/output section 225, an A/D converter 226, a clock, etc. In the present embodiment, various types of data, programs, etc., necessary for detection of ammonia concentration, etc., are stored in the ROM 223 of the ECU 221, and various types of processes are executed by the CPU 222.

The ECU 221 is electrically connected to the gas sensor control apparatus 300 of the multi-gas sensor apparatus 400. The ECU 221 obtains (receives), as needed, various types of data (information) necessary for the ammonia concentration detection process from the microcomputer (SCU) 60. The various types of data include the first ammonia electromotive force EMF1 and the second ammonia electromotive force EMF2 detected by the ammonia sensor section 42 (the first ammonia sensor section 42x and the second ammonia sensor section 42y) of the multi-gas sensor apparatus 400 and the first pumping current Ip1 detected by the first pumping cell 2.

Notably, the pressure sensor 500 is mounted on the exhaust pipe 502 at a position between the DPF 504 and the SCR catalyst 505 as in the first embodiment (see FIG. 5). The result of detection by the pressure sensor 500 is stored in the ROM (EPROM, EEPROM, etc.) 223 of the ECU 221. The CPU 222 of the ECU 221 retrieves the pressure information representing the pressure of the gas under measurement from the ROM 223 when necessary. As described above, the ECU 221 obtains the pressure information (detection result) representing the pressure of the gas under measurement from the pressure sensor 500, which is an external device.

Here, a process will be described for detecting the ammonia concentration in the gas under measurement by utilizing the first ammonia electromotive force EMF1 detected by the first ammonia sensor section 42x of the multi-gas sensor apparatus 400, the first pumping current Ip1, etc.

Figure 10:
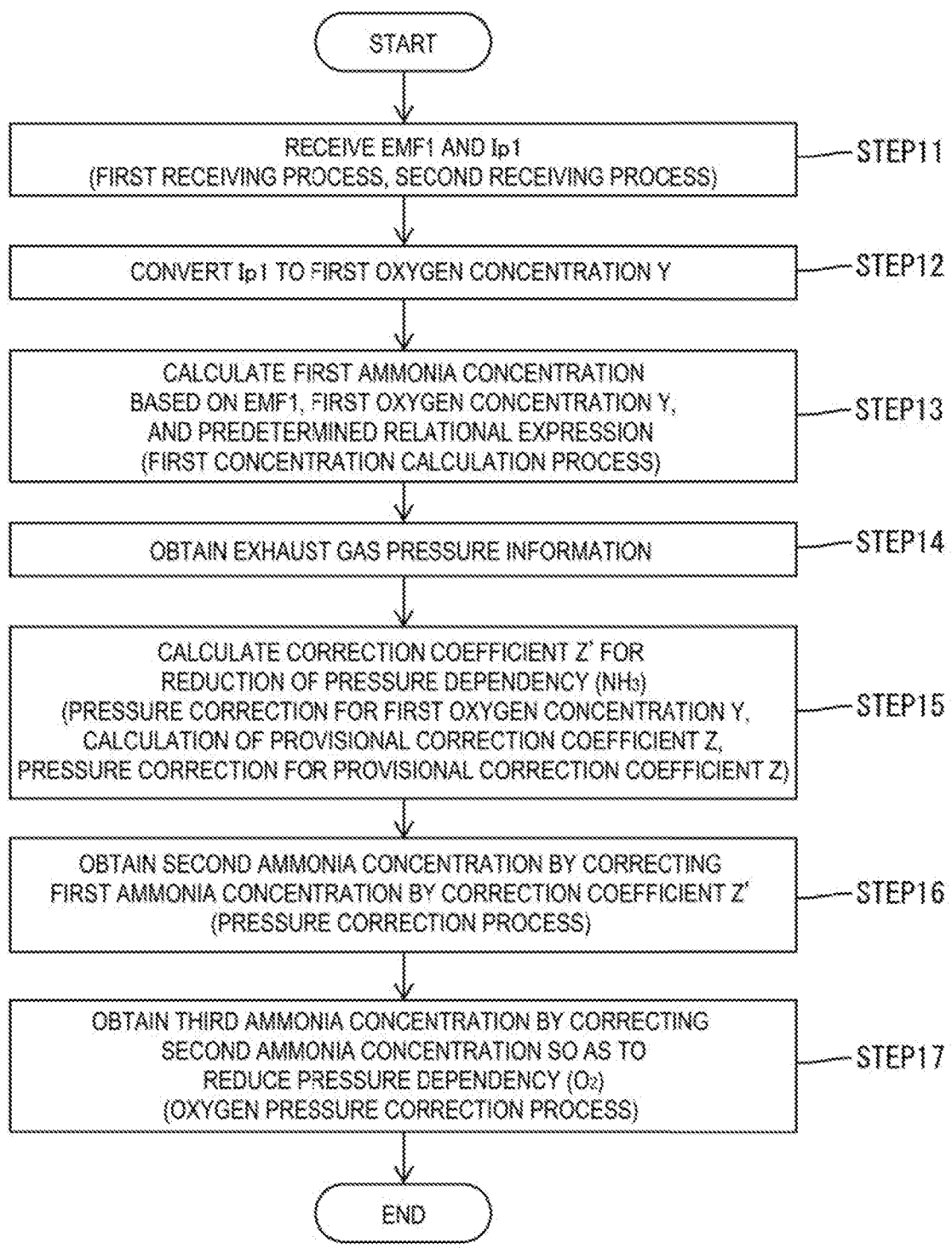
FIG. 10 is a flowchart showing the details of an ammonia concentration detection process in an ECU.

FIG. 10 is a flowchart showing the details of the ammonia concentration detection process in the ECU 221. As shown in STEP 11 to STEP 13 of FIG. 10, the first ammonia concentration is obtained by executing the same processes as those in the above-described first embodiment, although the processes are executed in the CPU 222 of the ECU 221.

In STEP 14 of FIG. 10, the CPU 222 retrieves the pressure information from the ROM 223, the pressure information representing the pressure of the exhaust gas (the gas under measurement) detected by the pressure sensor 500. Thus, the pressure information representing the pressure (absolute pressure) of the exhaust gas is obtained.

Also, as shown in STEP 15 to STEP 17 of FIG. 10, the same processes as those in the above-described first embodiment are performed, although the processes are executed in the CPU 222 of the ECU 221. As a result, the third ammonia concentration is finally obtained. The third ammonia concentration is the ammonia concentration in the gas under measurement determined by mitigating the influence of the pressure of the gas under measurement on ammonia concentration and the influence of the pressure of the gas under measurement on oxygen concentration.

As described above, an ammonia concentration detection process similar to the ammonia concentration detection process in the first embodiment may be performed in the ECU 221.

Third Embodiment

Next, a third embodiment of the present invention will be described with reference to FIG. 11, etc. In the present embodiment, the process for detecting the ammonia concentration in the gas under measurement is performed in the microcomputer (SCU) of the multi-gas sensor apparatus as in the first embodiment. However, in the ammonia concentration detection process for the present embodiment, the oxygen pressure correction for mitigating the influence of the pressure of the gas under measurement on oxygen concentration is not performed, although the pressure correction process is performed in order to mitigate the influence of the pressure of the gas under measurement on ammonia concentration.

Figure 11:
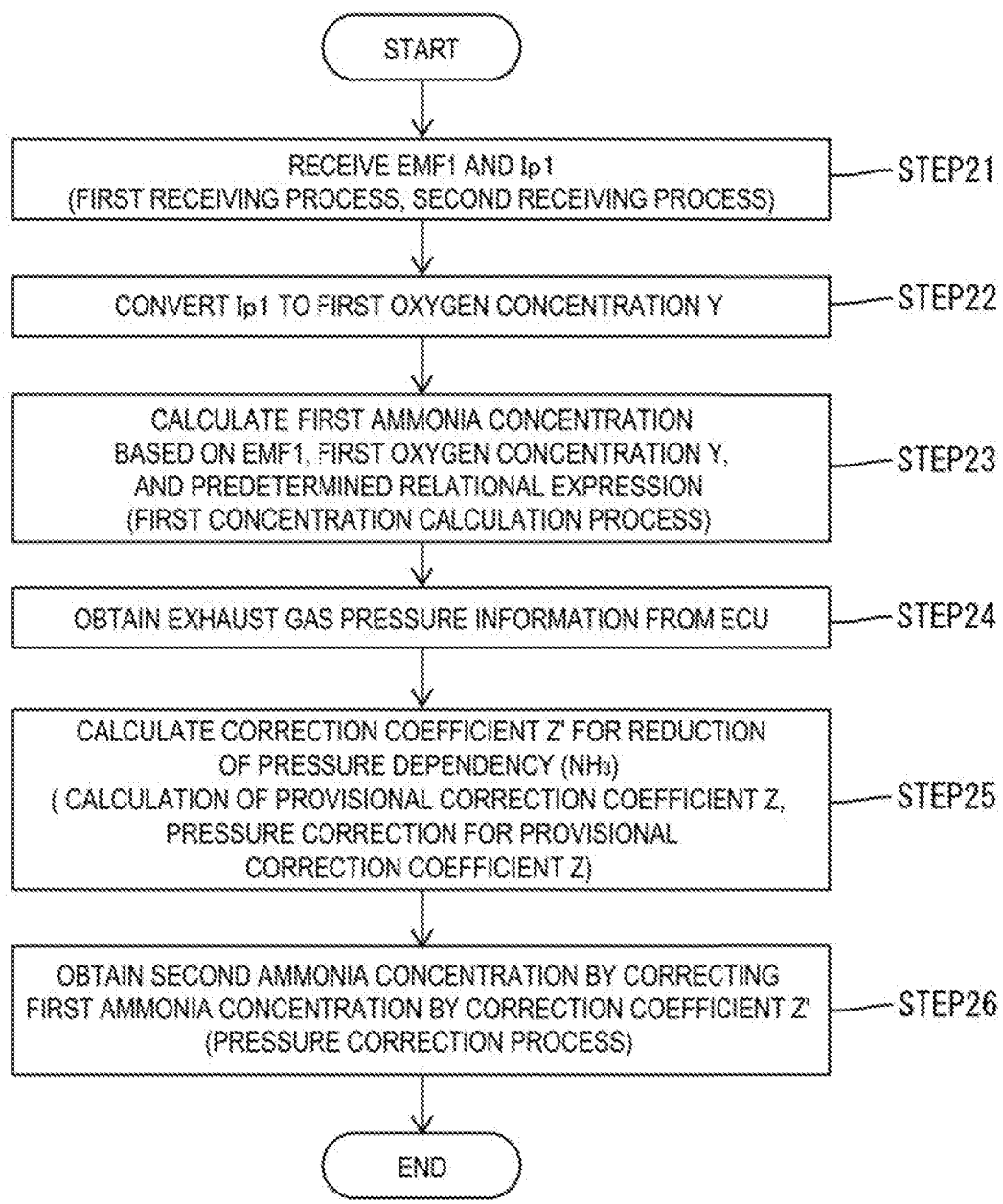
FIG. 11 is a flowchart showing the details of an ammonia concentration detection process according to a third embodiment.

FIG. 11 is a flowchart showing the details of the ammonia concentration detection process according to the third embodiment. As shown in STEP 21 to STEP 24 of FIG. 11, the same processes as those in STEP 1 to STEP 4 of the first embodiment (see FIG. 4) are executed in the CPU of the microcomputer (SCU).

Also, as shown in STEP 25 of FIG. 11, in the case of the present embodiment as well, the correction coefficient Z' is calculated as in STEP 5 of the first embodiment. However, in the present embodiment, since the influence of the pressure of the gas under measurement on oxygen concentration is not taken into consideration, the pressure correction for the first oxygen concentration Y using the above-described relational expression (1) is not performed for calculating the provisional correction coefficient Z. Therefore, the "(second oxygen concentration) Y'" in the above-described relational expression (2) for calculating the provisional correction coefficient Z is replaced with the "(first oxygen concentration) Y." Also, the "(second oxygen concentration) Y'" in the above-described relational expression (3) for calculating the correction coefficient Z' is replaced with the "(first oxygen concentration) Y."

Subsequently, as shown in STEP 26 of FIG. 11, the first ammonia concentration is corrected using the correction coefficient Z' as in STEP 6 of the first embodiment. As a result, the second ammonia concentration; i.e., the ammonia concentration determined by mitigating the influence of the pressure of the gas under measurement on ammonia concentration, is obtained.

As described above, in the case where the influence of the pressure of the gas under measurement on oxygen concentration is not required to be taken into consideration, only the pressure correction process (STEP 26) for mitigating the influence of the pressure of the gas under measurement on ammonia concentration may be performed.

The first pumping cell of the multi-gas sensor apparatus of the present embodiment pumps oxygen out of and into the gas under measurement (exhaust gas) introduced from the outside (the interior of the exhaust pipe) into the first measurement chamber through the porous protection layer and the first diffusion resistor element as in the first embodiment. In other embodiments in which the first measurement chamber communicates directly with the outside without intervention of the first diffusion resistor element, etc., it is unnecessary to consider the influence of the pressure of the gas under measurement on oxygen concentration. Therefore, the oxygen pressure correction process for mitigating the influence of the pressure of the gas under measurement on oxygen concentration may be performed as the need arises.

Fourth Embodiment

Next, a fourth embodiment of the present invention will be described with reference to FIG. 12, etc. In the present embodiment, the process for detecting the ammonia concentration in the exhaust gas is performed in the ECU (internal combustion engine control apparatus) as in the second embodiment. Also, in the ammonia concentration detection process for the present embodiment, only the pressure correction process for the purpose of mitigating the influence of the pressure of the gas under measurement on ammonia concentration is performed as in the third embodiment.

Figure 12:
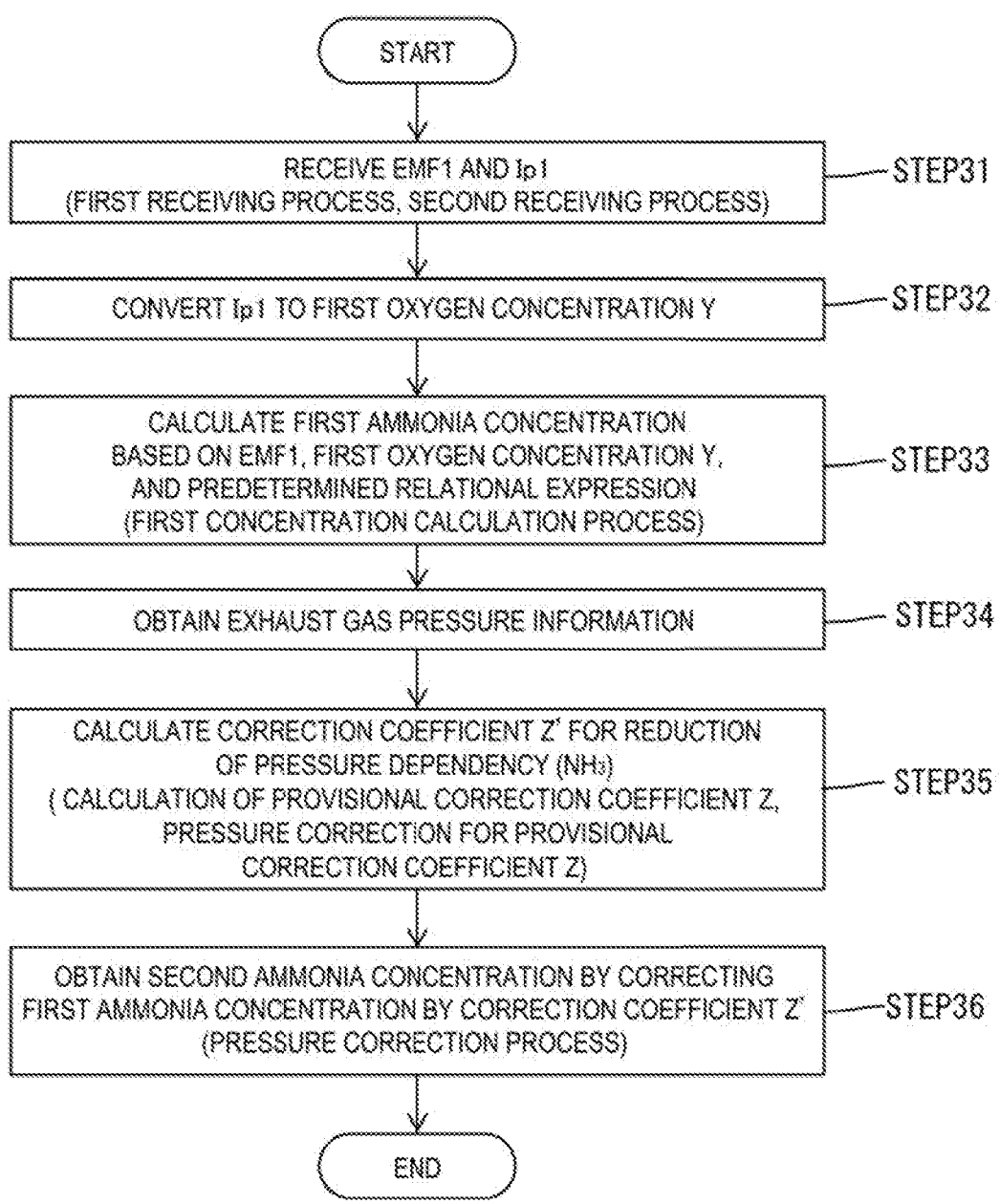
FIG. 12 is a flowchart showing the details of an ammonia concentration detection process according to a fourth embodiment.

FIG. 12 is a flowchart showing the details of the ammonia concentration detection process according to the fourth embodiment. As shown in STEP 31 to STEP 33 of FIG. 12, the first ammonia concentration is obtained by executing the same processes as those in the above-described third embodiment, although the processes are executed in the CPU of the ECU.

In STEP 34 of FIG. 12, the CPU of the ECU retrieves the pressure information from the ROM (EPROM, EEPROM, etc.) of the ECU, the pressure information representing the pressure of the exhaust gas (the gas under measurement) detected by the pressure sensor. Thus, the pressure information representing the pressure (absolute pressure) of the exhaust gas is obtained (see FIG. 10, same as the STEP 14 of the second embodiment).

Also, as shown in STEP 35 and STEP 36 of FIG. 12, the same processes as those in the above-described third embodiment are performed, although the processes are executed in the CPU of the ECU. As a result, the second ammonia concentration; i.e., the ammonia concentration in the gas under measurement determined by mitigating the influence of the pressure of the gas under measurement on ammonia concentration, is finally obtained.

As described above, an ammonia concentration detection process similar to the ammonia concentration detection process in the fourth embodiment may be performed in the ECU (internal combustion engine control apparatus).

Fifth Embodiment

Next, a fifth embodiment of the present invention will be described with reference to FIG. 13, etc. In the present embodiment, the process for detecting the ammonia concentration in the gas under measurement is performed in the microcomputer (SCU) of the multi-gas sensor apparatus as in the first embodiment. However, in the ammonia concentration detection process for the present embodiment, a simultaneous correction process is performed so as to simultaneously mitigate the influence of the pressure of the gas under measurement on ammonia concentration and the influence of the pressure of the gas under measurement on oxygen concentration.

Figure 13:
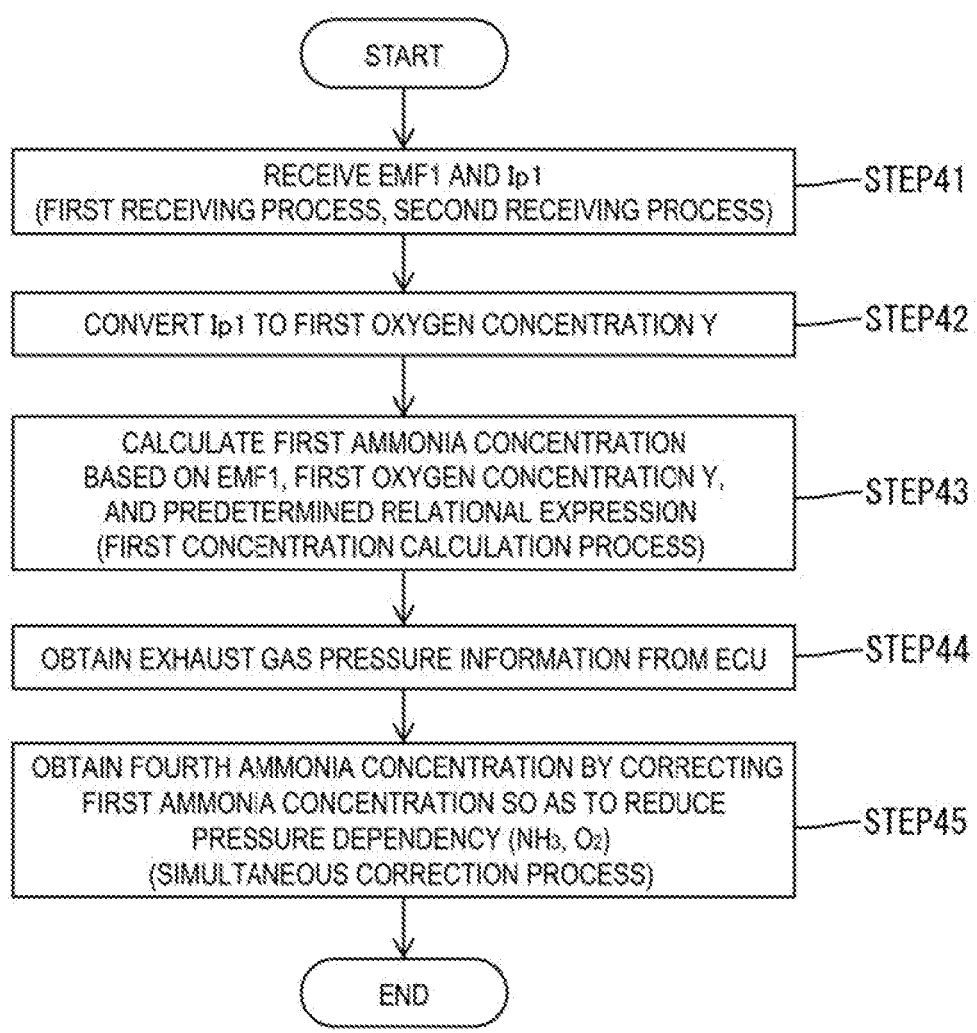
FIG. 13 is a flowchart showing the details of an ammonia concentration detection process according to a fifth embodiment.

FIG. 13 is a flowchart showing the details of the ammonia concentration detection process according to the fifth embodiment. As shown in STEP 41 to STEP 44 of FIG. 13, the same processes as those in STEP 1 to STEP 4 of the first embodiment (see FIG. 4) are executed in the CPU of the microcomputer (SCU).

Subsequently, in the present embodiment, the simultaneous correction process is performed in STEP 45 of FIG. 13 in place of STEP 5 to STEP 7 (FIG. 4, the pressure correction process, the oxygen pressure correction process, etc.) of the first embodiment. In this simultaneous correction process, a simultaneous correction coefficient α for the purpose of mitigating the influence of the pressure of the gas under measurement on ammonia concentration and mitigating the influence of the pressure of the gas under measurement on oxygen concentration is obtained based on the pressure information obtained in STEP 44 and representing the pressure (absolute pressure) of the exhaust gas (the gas under measurement).

The simultaneous correction coefficient α is obtained using a relational expression determined based on for example, the results of the above-described ammonia detection test 1, ammonia detection test 2, and oxygen detection test. The first ammonia concentration calculated in STEP 43 is corrected using the simultaneous correction coefficient α, whereby a fourth ammonia concentration is obtained. The fourth ammonia concentration is the ammonia concentration in the gas under measurement determined by mitigating the influence of the pressure of the gas under measurement on ammonia concentration and the influence of the pressure of the gas under measurement on oxygen concentration.

As described above, mitigation of the influence of the pressure of the gas under measurement on ammonia concentration and mitigation of the influence of the pressure of the gas under measurement on oxygen concentration may be performed by a single process. In the case where the processes for correcting the first ammonia concentration are merged into a single process, the processing load of the CPU can be reduced.

Sixth Embodiment

Next, a sixth embodiment of the present invention will be described with reference to FIG. 14, etc. In the present embodiment, the process for detecting the ammonia concentration in the exhaust gas is performed in the ECU (internal combustion engine control apparatus) as in the second embodiment. Also, in the ammonia concentration detection process for the present embodiment, the simultaneous correction process for simultaneously mitigating the influence of the pressure of the gas under measurement on ammonia concentration and the influence of the pressure of the gas under measurement on oxygen concentration is performed as in the fifth embodiment.

Figure 14:
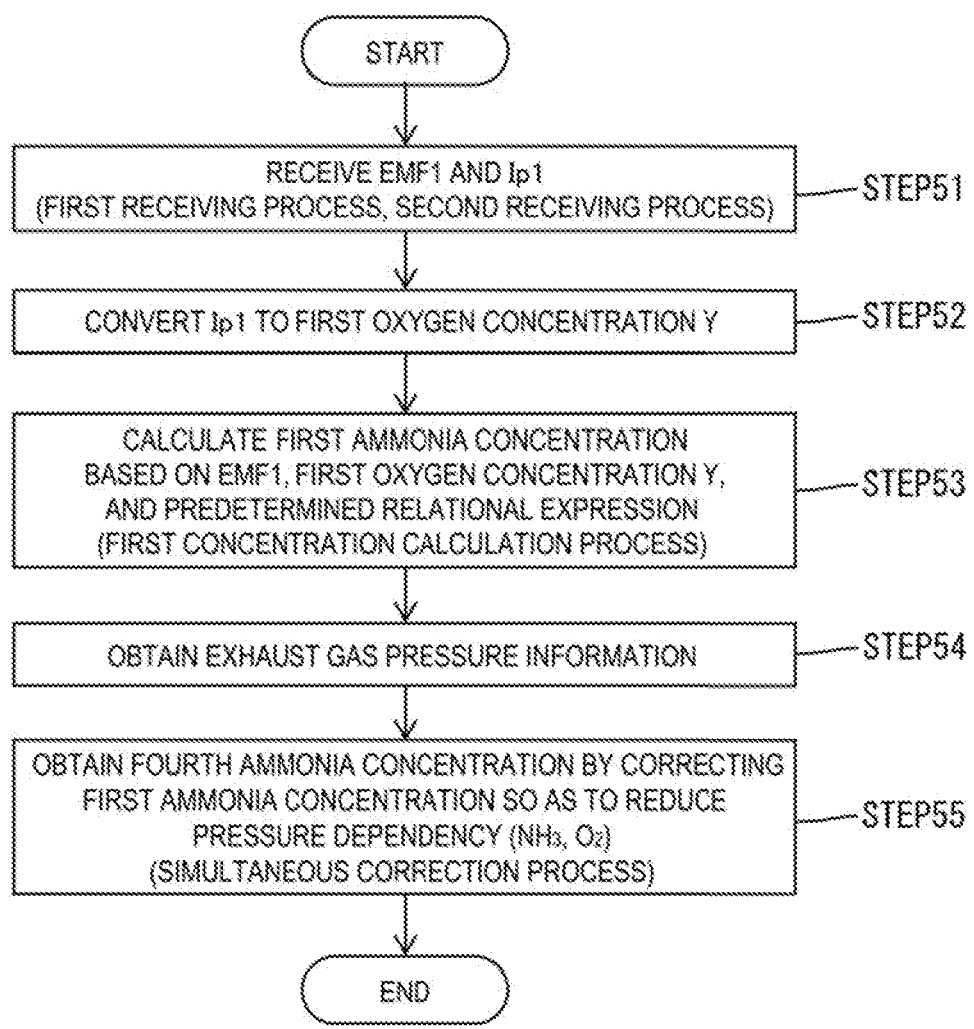
FIG. 14 is a flowchart showing the details of an ammonia concentration detection process according to a sixth embodiment.

FIG. 14 is a flowchart showing the details of the ammonia concentration detection process according to the sixth embodiment. As shown in STEP 51 to STEP 54 of FIG. 14, the same processes as those in STEP 11 to STEP 14 of the second embodiment (see FIG. 10) are executed in the CPU of the ECU.

Subsequently, in the present embodiment, in STEP 55 of FIG. 14, a simultaneous correction process similar to that in the fifth embodiment is performed in the CPU of the ECU, whereby the fourth ammonia concentration (i.e., the ammonia concentration determined by mitigating the influence of the pressure of the gas under measurement on ammonia concentration and the influence of the pressure of the gas under measurement on oxygen concentration) is obtained.

As described above, an ammonia concentration detection process similar to the ammonia concentration detection process in the fifth embodiment may be performed in the ECU (internal combustion engine control apparatus).

Other Embodiments

The present invention is not limited to the embodiments having been described with reference to the drawings, and, for example, the following embodiments fall within the technical scope of the present invention.

(1) In the above-described embodiments, a diesel engine is shown as an example of the internal combustion engine. However, the gas sensor control apparatus, the gas sensor apparatus, and the internal combustion engine control apparatus of the present invention may be applied to a gasoline engine.

(2) In the above-described embodiments, a multi-gas sensor apparatus having two mixed-potential-type ammonia sensor sections is shown as an example. However, this does not limit the present invention, and the present invention may be applied to, for example, a gas sensor apparatus including a single mixed-potential-type ammonia sensor section.

(3) In the above-described embodiments, the pressure sensor mounted on the exhaust pipe at a location between the DPF and the SCR catalyst is used. However, this does not limit the present invention, and a pressure sensor disposed at a different location may be used.

(4) In the above-described embodiments, a multi-gas sensor apparatus including an oxygen detection section and an ammonia detection section (namely, an apparatus in which the oxygen detection section and the ammonia detection section are integrated) is unitized. However, this does not limit the present invention, and an apparatus in which the oxygen detection section and the ammonia detection section are separated and independent from each other may be used.

(5) In the above-described embodiments, the correction coefficient Z' calculated using the pressure information representing the pressure of the gas under measurement, the relational expressions (1) to (3), etc., is used in the process (pressure correction process) for mitigating the influence of the pressure of the gas under measurement on ammonia concentration. However, the present invention is not limited thereto. In other embodiments, for example, the relation between the first ammonia concentration and the pressure of the gas under measurement may be prepared beforehand in the form of a table, and the pressure correction process may be performed using the table. Similarly, each of the oxygen pressure correction process and the simultaneous correction process may be performed by using a table prepared beforehand.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application claims priority from Japanese Patent Application Nos. 2019-166843 and 2020-125048 filed Sep. 13, 2019 and Jul. 22, 2020, respectively, the above noted applications incorporated herein by reference in their entirety.

What is claimed is:

1. A gas sensor control apparatus comprising a control section that executes:
    a first receiving process for receiving a first detection result output from a mixed-potential-type ammonia detection section for detecting ammonia contained in a gas under measurement, the first detection result corresponding to the concentration of the ammonia,
    a second receiving process for receiving a second detection result output from an oxygen detection section for detecting oxygen contained in the gas under measurement, the second detection result corresponding to the concentration of the oxygen,
    a first concentration calculation process for calculating, as a first ammonia concentration, the concentration of ammonia contained in the gas under measurement based on the first detection result and the second detection result, and
    a pressure correction process for correcting the first ammonia concentration, based on pressure information obtained from an external device and representing pressure of the gas under measurement, so as to mitigate an influence of pressure of the gas under measurement on the first ammonia concentration, thereby obtaining a second ammonia concentration of the gas under measurement.

2. The gas sensor control apparatus as claimed in claim 1, wherein the pressure correction process is a process for obtaining the second ammonia concentration by correcting the first ammonia concentration using a correction coefficient based on the pressure information.

3. The gas sensor control apparatus as claimed in claim 1, wherein, when the detected oxygen concentration is influenced by the pressure of the gas under measurement, the control section executes an oxygen pressure correction process for correcting the second ammonia concentration based on the pressure information representing the pressure of the gas under measurement so as to mitigate an influence of the pressure, thereby obtaining a third ammonia concentration of the gas under measurement.

4. The gas sensor control apparatus as claimed in claim 1, wherein, when the detected oxygen concentration is influenced by the pressure of the gas under measurement, the control section executes, instead of the pressure correction process, a simultaneous correction process for correcting the first ammonia concentration based on the pressure information representing the pressure of the gas under measurement so as to mitigate an influence of the pressure of the gas under measurement on the first ammonia concentration and an influence of the pressure of the gas under measurement on the detected oxygen concentration, thereby obtaining a fourth ammonia concentration of the gas under measurement.

5. A gas sensor apparatus comprising:
    a mixed-potential-type ammonia detection section for detecting ammonia contained in a gas under measurement;
    an oxygen detection section for detecting oxygen contained in the gas under measurement; and
    a gas sensor control apparatus as claimed in claim 1.

6. An internal combustion engine control apparatus for controlling an operation state of an internal combustion engine, the internal combustion engine control apparatus comprising a control section that executes:
- a first receiving process for receiving a first detection result output from a mixed-potential-type ammonia detection section for detecting ammonia contained in a gas under measurement discharged from the internal combustion engine, the first detection result corresponding to the concentration of the ammonia detected by the mixed-potential-type ammonia detection section,
- a second receiving process for receiving a second detection result output from an oxygen detection section for detecting oxygen contained in the gas under measurement, the second detection result corresponding to the concentration of the oxygen,
- a first concentration calculation process for calculating, as a first ammonia concentration, the concentration of ammonia contained in the gas under measurement based on the first detection result and the second detection result, and
- a pressure correction process for correcting the first ammonia concentration, based on pressure information obtained from an external device and representing pressure of the gas under measurement, so as to mitigate an influence of pressure of the gas under measurement on the first ammonia concentration, thereby obtaining a second ammonia concentration of the gas under measurement.

7. The internal combustion engine control apparatus as claimed in claim 6, wherein the pressure correction process is a process for obtaining the second ammonia concentration by correcting the first ammonia concentration using a correction coefficient based on the pressure information.

8. The internal combustion engine control apparatus as claimed in claim 6, wherein, when the detected oxygen concentration is influenced by the pressure of the gas under measurement, the control section executes an oxygen pressure correction process for correcting the second ammonia concentration based on the pressure information representing the pressure of the gas under measurement so as to mitigate an influence of the pressure, thereby obtaining a third ammonia concentration of the gas under measurement.

9. The internal combustion engine control apparatus as claimed in claim 6, wherein, when the detected oxygen concentration is influenced by the pressure of the gas under measurement, the control section executes, instead of the pressure correction process, a simultaneous correction process for correcting the first ammonia concentration based on the pressure information representing the pressure of the gas under measurement so as to mitigate an influence of the pressure of the gas under measurement on the first ammonia concentration and an influence of the pressure of the gas under measurement on the detected oxygen concentration, thereby obtaining a fourth ammonia concentration of the gas under measurement.

* * * * *